United States Patent [19]
Lynnworth et al.

[11] 4,320,659
[45] Mar. 23, 1982

[54] ULTRASONIC SYSTEM FOR MEASURING FLUID IMPEDANCE OR LIQUID LEVEL

[75] Inventors: Lawrence C. Lynnworth; John L. Seger, both of Waltham; James E. Bradshaw, Tyngsboro, all of Mass.

[73] Assignee: Panametrics, Inc., Waltham, Mass.

[21] Appl. No.: 111,466

[22] Filed: Jan. 11, 1980

Related U.S. Application Data

[63] Continuation-in-part of Ser. No. 881,754, Feb. 27, 1978, abandoned.

[51] Int. Cl.³ .................................................. G01N 29/02
[52] U.S. Cl. ........................................... 73/589; 73/53; 73/290 V
[58] Field of Search ............... 73/53, 290 V, 589, 592, 73/597, 599, 629, 644

[56] References Cited
U.S. PATENT DOCUMENTS
2,966,058 12/1960 McSkimin .............................. 73/597
3,512,400 5/1970 Lynnworth ........................... 73/597

FOREIGN PATENT DOCUMENTS
648023 9/1962 Canada.

OTHER PUBLICATIONS
J. and H. Krautkramer-*Ultrasonic Testing of Materials*, 2nd Ed., Springer-Verlag, pp. 569-572 (1977).
L. Lynnworth, "Industrial Application of Ultrasound-A Review II. Measurements, Tests and Process Control Using Low Intensity Ultrasound", IEEE Transactions on Sonics and Ultrasonics, vol. SU-22(2) pp. 71-100, Mar. 1975.
A. E. Arave, "An Ultrasonic Void Fraction Detector Using Compressional Stress Waves in a Wire Helix", Idaho Nuclear Corporation, IN-1441, Oct. 1970.
A. E. Arave, "An Ultrasonic Liquid Level Detector Using Shear Wave Attenuation in a Bar", Idaho Nuclear Corporation, IN-1442, Nov. 1970.
A. E. Arave, "Ultrasonic Liquid Level Detector Using Surface Wave Attenuation in a Tube", Aerojet Nuclear Company, ANCR-1047, Jan. 1972.

*Primary Examiner*—Charles A. Ruehl
*Attorney, Agent, or Firm*—Kenway & Jenney

[57] ABSTRACT

An ultrasonic system that measures either the impedance of a fluid or liquid level utilizes moderately directional, bulk SV mode sound waves generated by a transducer and propagated in a homogeneous, flaw-free solid member. The SV wave propagates in the solid along a zigzag path that reflects at a solid-fluid interface in at least two areas and at an angle of incidence that exceeds the first critical angle by at least five degrees and is less than the second critical angle by at least ten degrees. The attenuated amplitude of the wave due to acoustic coupling between the solid and the fluid measures the impedance or an impedance related parameter of the fluid. The system preferably includes a second acoustic path that serves as a reference to compensate for changes in parameters such as temperature, the nature of the fluid, the transducer, the transducer coupling, and residues or corrosion at the solid-fluid interface. In another form, the reference mechanism is a series of reflections from notches in the solid member. For liquid level measurement desensitized to variations in the liquid impedance, the solid is an elongated member that is oriented at an oblique angle, or is parallel to, the surface of the liquid. Other liquid level measurement systems utilize multiple receivers or reflectors located at the points of reflection of the zigzag wave.

54 Claims, 43 Drawing Figures

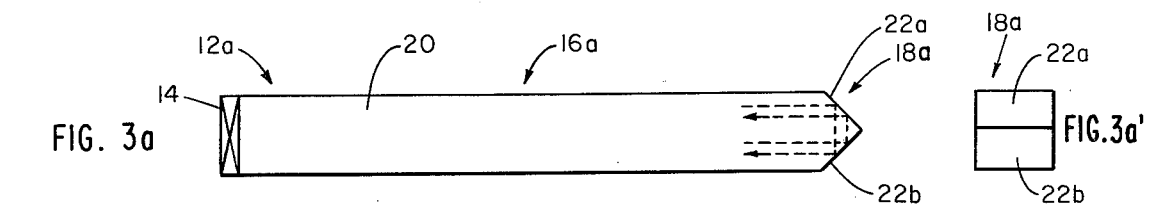
FIG. 3a    FIG. 3a'
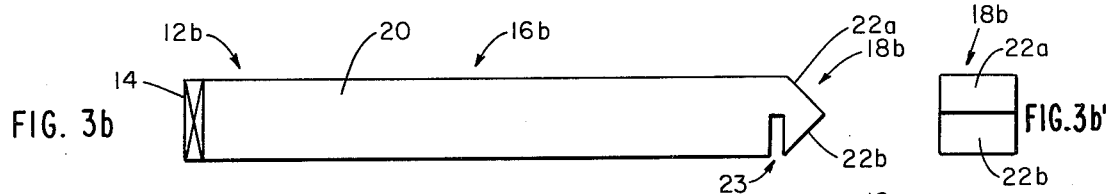
FIG. 3b    FIG. 3b'
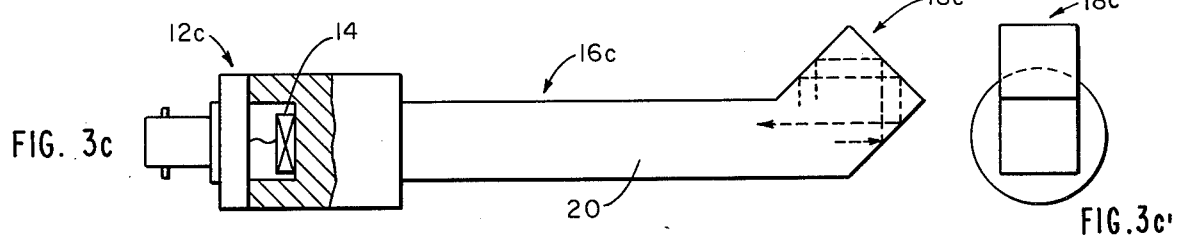
FIG. 3c    FIG. 3c'
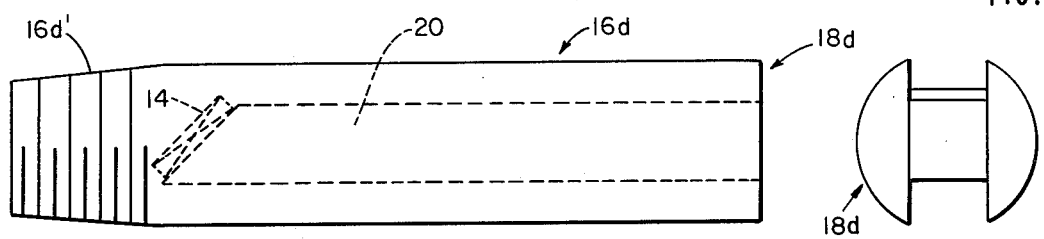
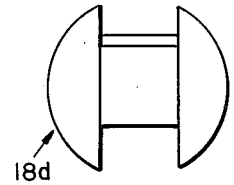
FIG. 3d    FIG. 3d'
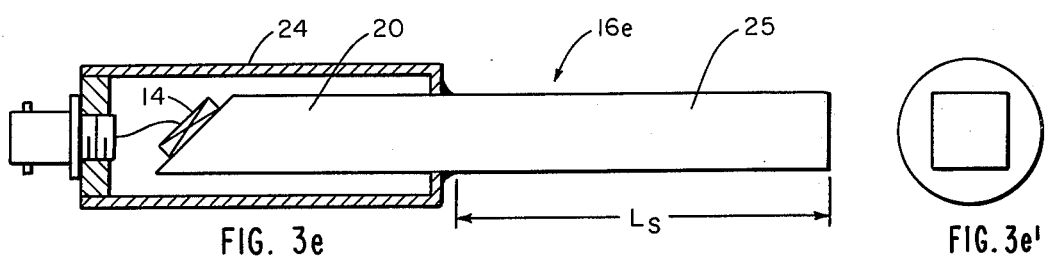
FIG. 3e    FIG. 3e'
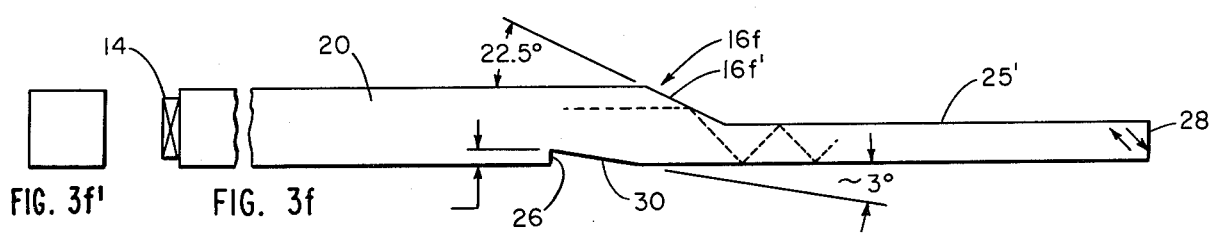
FIG. 3f'    FIG. 3f

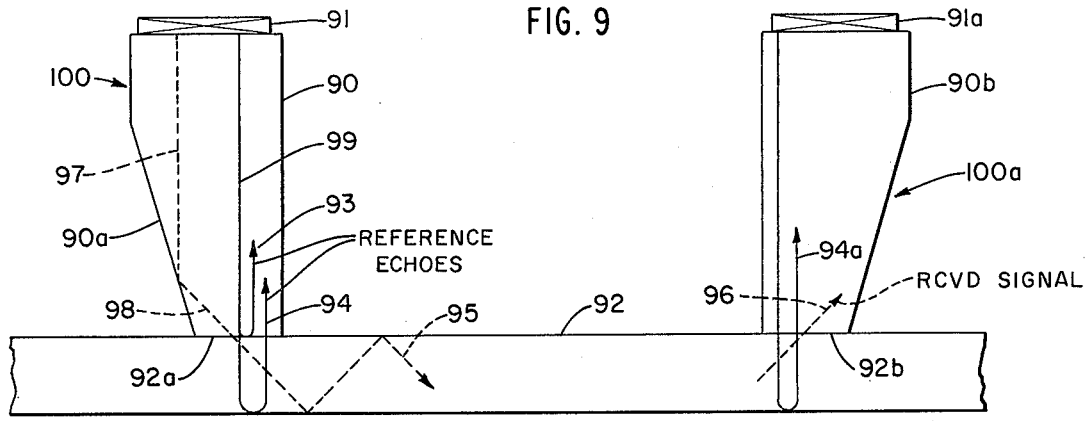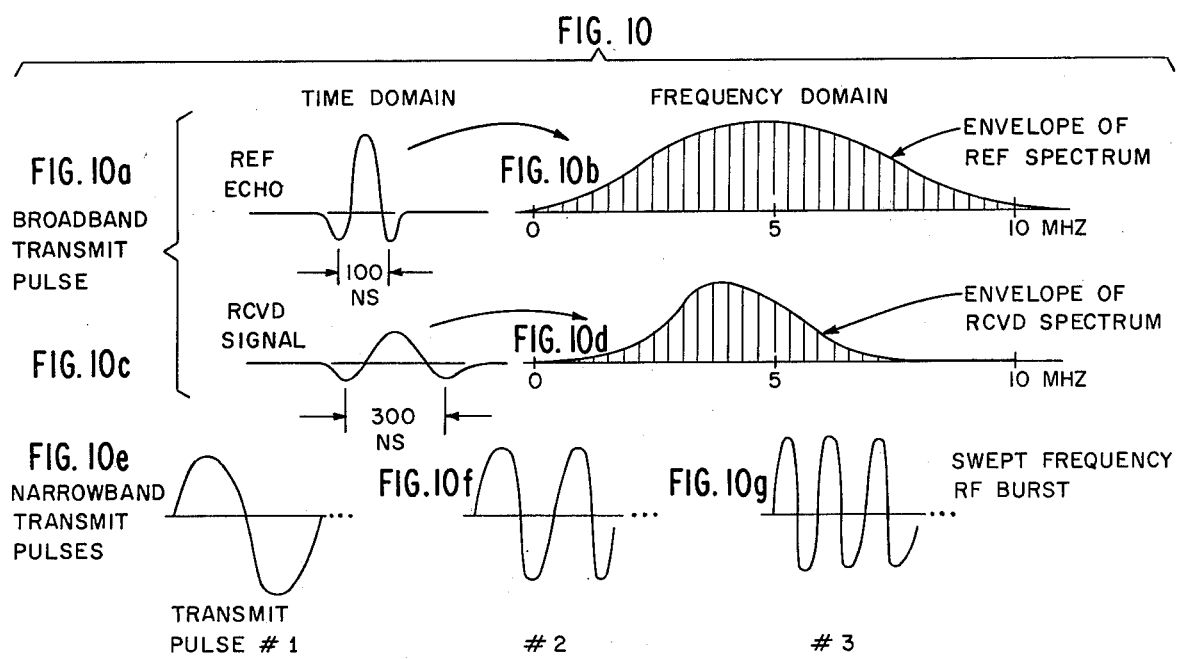

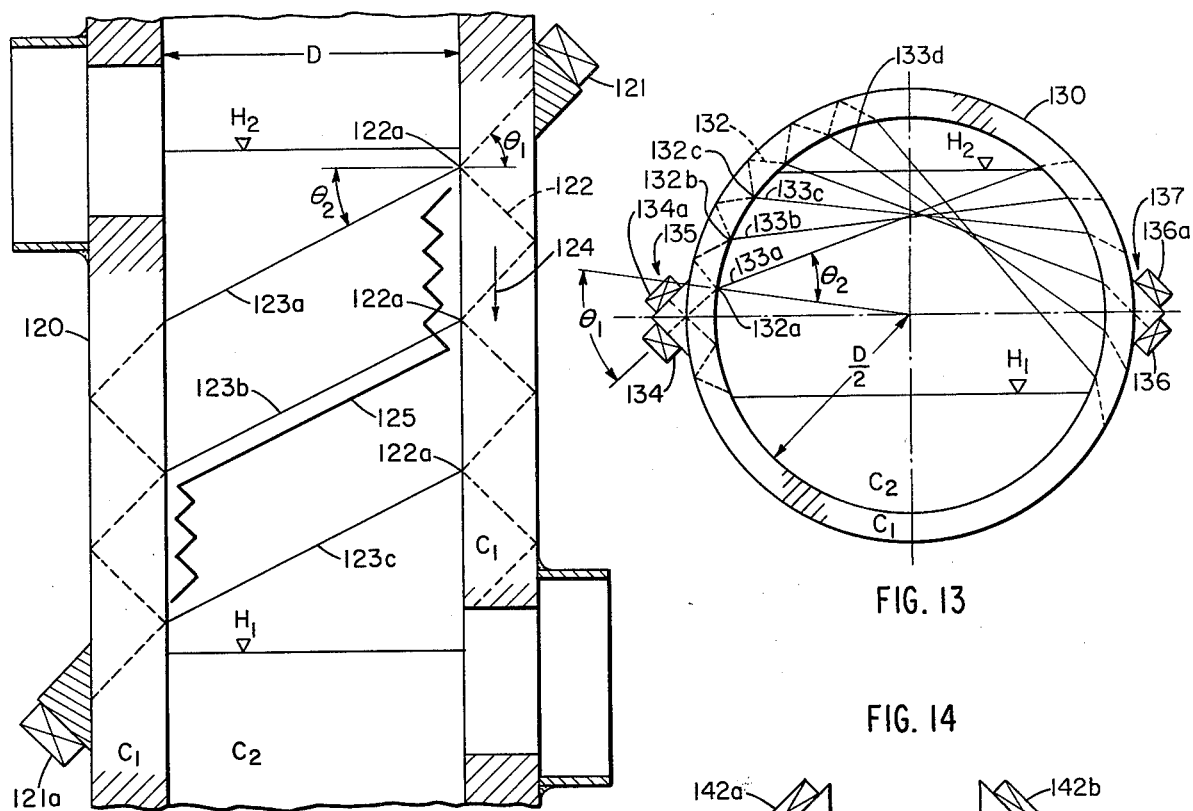
FIG. 12
FIG. 13
FIG. 14
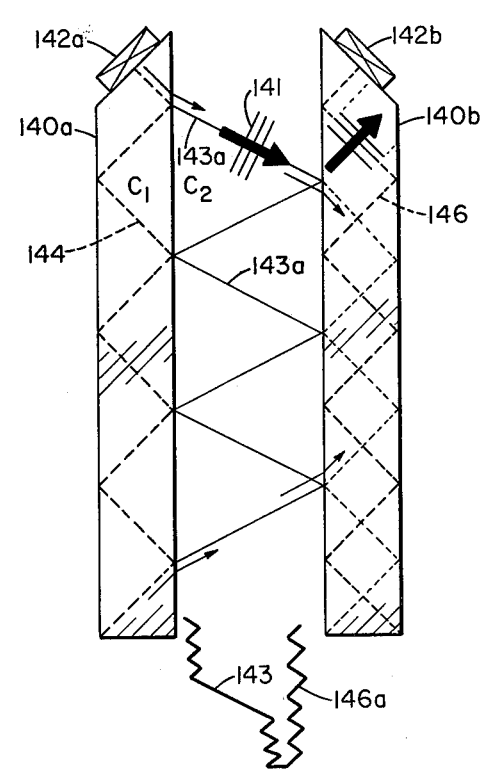

ULTRASONIC SYSTEM FOR MEASURING FLUID IMPEDANCE OR LIQUID LEVEL

This application is a continuation-in-part of U.S. Ser. No. 881,754 filed Feb. 27, 1978 now abandoned.

BACKGROUND OF THE INVENTION

This invention relates in general to ultrasonic measurement systems. More specifically, it relates to an ultrasonic system that (1) utilizes obliquely incident, vertically polarized shear mode (SV) energy propagated in a solid to measure the acoustic impedance and related properties of an adjacent fluid, typically a liquid, and (2) in its preferred form measures a selected parameter of the fluid—its impedance or level—while rendering the measurement substantially insensitive to variations in other parameters affecting the transmission of the interrogating sound wave.

In both scientific and industrial applications ultrasonic techniques have been used to measure the acoustic impedance Z of a liquid or related parameters such as liquid level in a container, density in a single and two-phase liquids, and mass flow rate. In a single phase liquid, the density is given by Z/c, the impedance divided by the sound speed. The mass flow rate of liquids such as aircraft fuel is proportional to the product of the impedance and the fuel Mach number V/c, the flow velocity divided by the sound speed. The Mach number is readily determined by standard ultrasonic techniques using Doppler flowmeters, beam drift flowmeters or upstream/downstream contrapropagating transmission flowmeters.

Many common commercial systems for measuring impedance or related parameters utilize longitudinal (L) ultrasonic energy directed at a normal incidence to the fluid under interrogation. In one system a single beam of L wave energy is directed vertically downward into a container partly filled with a liquid to measure the liquid level, but confusion arises if foam is above the liquid. Another intrusive system, used principally to detect liquid level, transmits L wave energy between transducers across a rectangular recess formed in a side of a probe when the recess is immersed in the liquid. Energy is not transmitted when air or foam fill the recess. This device thus provides comparatively crude "liquid present" or "liquid not present" information. This prior art system is of course limited to applications where the intrusive transducers and their associated seals, bonds and electrical connections can operate in the environment in and around the liquid which can include extremely high degrees of temperature, pressure and radiation or chemically corrosive substances.

In two 1955 articles J. Kritz describes a mass flowmeter that utilizes the reflection coefficient of L waves at normal incidence to an interface of a quartz transducer and aircraft fuel to measure the impedance of the fuel. The fuel "loads" the transducer either directly by immersion or indirectly through a plate of low attenuation material as described in his U.S. Pat. No. 2,869,375. A similar approach is described by W. Welkowitz in U.S. Pat. No. 2,959,054. One of the present applicants also developed techniques for measuring acoustic impedance with longitudinal waves propagated in special buffer rods or thin walls to interrogate a liquid at a liquid-solid interface with normal incidence. One problem with these techniques is that the transducer and/or its backing interacts with the reflected wave too often, extracting a significant fraction of the energy. As a result, the measurement is too sensitive to variables associated with the transducer and its coupling. Examples of configurations of this type are described in "Industrial Applications of Ultrasound-A Review II. Measurements, Tests and Process Control Using Low Intensity Ultrasound" by L. Lynnworth in IEEE Transactions on Sonics and Ultrasonics, Vol. SU-22(2) pp. 71-101, March, 1975. Pages 82 and 83 of that article also describe the work of Moore and McSkimin using normal incidence shear wave complex reflectance. Additional general references on ultrasonic liquid level approaches include J. and H. Krautkramer, *Ultrasonic Testing of Materials*, 2nd Ed., Springer-Verlag, pp. 569–572 (1977) and Mason and Thurston (ed.), *Physical Acoustics*, Vol. 14, pp. 458–462 (1979), contained in Chap. 5 which was authored by one of the applicants.

U.S. Pat. No. 2,996,058 to McSkimin describes the use or horizontally polarized shear mode (SH) waves propagated in a trapezoidally-sectioned block of fused silica to measure the viscosity and elasticity of a liquid specimen resting on a top surface of the block. The SH waves are incident on the top surface at an incidence angle of approximately 79 degrees. The phase shift and attenuation of these waves, due to absorption in the liquid, provides the measure of its viscosity. This system has numerous drawbacks. The top surface of the block must be very flat and smooth and the liquid sample volumes are small and the interaction between the ultrasonic energy and the liquid is confined to a single, small area. These limitations make the apparatus practical only for laboratory use. Further, the McSkimin arrangement is not useful for the many liquids with low viscosities, that is, less than 1 centipoise, unless very high frequencies are used, e.g. approximately 10 to 100 MHz. At these frequencies, however, particularly the more useful ones closer to the upper end of the range, attenuation due to probe losses becomes significant. While McSkimin uses a second interrogating beam which can be SV mode energy, this beam is merely a reference beam to compensate for troublesome experimental (temperature) variations; it does not necessarily interrogate the liquid sample.

Shear waves propagated in magnetostrictive probes having sensors in the form of a helix, circular tube or solid rectangular rod have been used by A. E. Arave to investigate the attenuating affects of surrounding water at various temperatures. This work is reported in "Idaho Nuclear Corporation Reports, IN-1441 and 1442 (1970)" and "Aerojet Nuclear Corp. Report ANCR-1047 (1972)." These probes, however, are characterized by cross sections that are small (1 or several mm) compared to the wave-length and the sound energy, if in the shear mode, is at substantially normal incidence. Because of these small probe dimensions, the interrogating energy is a guided wave, that is, the velocity and mode of propagation of the wave depends on the boundary conditions, in contrast to bulk waves which are not so affected. While Arave's arrangements respond to the acoustic impedance of the liquid, the interaction is unpredictable because of uncontrolled mode conversion (due to sharp curvature) and other uncontrolled losses due to the immersion of a guided wave having an ill defined angular arrangement or impure modal content. The results were also found to be undesirably sensitive to transduction efficiency, which is temperature-dependent.

In contrast to the foregoing systems characterized by interrogation at normal incidence or ultrasonic energy in the longitudinal or SH modes, U.S. Pat. No. 3,512,400 to Lynnworth describes the use of SV mode waves that follow a zigzag pattern in a solid. This system, however, is designed to detect flaws in the solid, not to interrogate a fluid adjacent the solid. Moreover, in flaw detection is is often desirable to operate even beyond the second critical angle and with short bursts of energy, typically a few cycles in duration.

Canadian Pat. No. 648,023 to Van Valkenburg and the Krautkramer book, cited above at p. 572, describe another ultrasonic measuring system using sound waves (which could be in the SV mode) to measure liquid level in a closed container. The illustrated system has a probe that is suspended vertically in the container and transmits the interrogating wave along a zigzag path. This arrangement, however, provides an accurate, unambiguous measure of liquid level only if the operating conditions are relatively ideal, that is, if the liquid and the probe are at a nearly constant temperature, the identity and characteristics (e.g. impedance, viscosity) of the liquid do not change, and other factors such as the residue deposits on the probe remain constant. Under non-ideal conditions, which are typical in commercial applications, the Van Valkenburg system will not produce reliable readings. For example, a 25% change in the impedance of the liquid held in the container can result in a 25% error in the measured level; seasonal, altitude or geographically induced changes in temperature T can result in comparable errors in the measured level (e.g., aircraft fuel tank liquid level). The Kritz article, for example, presents a graph showing large changes in fuel sound speeds as T is varied. Further, in a paper by Korycki et al., *Ultrasonics* 17, 166–174, July 1979, the acoustic impedance of a petroleum product, Hydrol 40 oil, is plotted in FIG. 12 as a function of pressure and temperature, for pressures from 0 to 200 MPa, and temperatures from 0 to 80° C. This graph shows that Hydrol's impedance varies over a 2:1 range, from 0.105 to 0.215 MN s m$^{-3}$. An uncompensated or not desensitized liquid level probe, calibrated for mid-range impedance, could easily yield liquid level readings with 40 to 50% errors at impedance extremes.

The Van Valkenburg patent, moreover, does not appreciate that a zigzag propagating SV wave will couple with the fluid to provide a reliable measure of the *impedance* of the fluid. In the Van Valkenburg arrangement, the measurement does not distinguish between attenuation due to the impedance of the probe, the impedance of the adjacent liquid(s), impedance ratios, or other factors such as variation in the transducer coupling or residues on the probe. This is reflected in the failure of this patent to provide general and sufficient guidelines for designs favorable to this coupling such as the frequency or other (e.g., polarization) characteristics of the wave, limits on the angles of incidence of the wave at the solid-fluid interface, and the structure of the probe, particularly for practical use in non-ideal conditions.

It is therefore a principal object of this invention to provide a practical ultrasonic system for measuring fluid impedance or liquid level that has an unambiguous, predictable and sensitive response.

Another principle object of the invention is to provide such a measuring system that isolates the measurement of a selected parameter and insulates the measurement from or compensates for variations in other parameters.

Another object is to provide a system for measuring two or more variables simultaneously or sequentially, such as fluid impedance, level, temperature, viscosity or viscosity range.

Another object is to provide an acoustic measuring system that does not immerse the transducers and which can interrogate an inaccessible fluid, fluids in one or two phases, and fluids having a wide range of viscosities.

Still another object is to provide a measuring system that can be readily designed for either a localized or distributed interrogation of a fluid at one or several surfaces and interrogation along paths with varying orientations.

A further object is to provide a measurement system that is readily applied to existing conduits and containers, including conduits and containers with curved walls.

Another object is to provide a measuring system that simplifies the compensation for changes in the probe such as its temperature.

Yet another object is to provide a measuring system that does not require special surface preparation and operates effectively despite thin layers of residue, corrosion, paint or the like adjacent the fluid under interrogation.

A still further object is to provide a measuring system that can measure liquid level under static or dynamic conditions including rapid fluctuation or turbulence.

Another object is to provide a measuring system that operates at frequencies that are not readily attenuated in common liquids.

SUMMARY OF THE INVENTION

An ultrasonic system that measures the acoustic impedance or related parameters of a fluid has a transducer or transducer assembly acoustically coupled to a solid member. The transducer generates sound energy waves in a vertically polarized shear (SV) mode. The frequency of the SV wave and the dimensions of the transducer and the solid medium are selected so that the waves are moderately directional and bulk, with no significant mode conversion, and minimal attenuation in the solid portion of the probe. The frequency is preferably in the range of 0.5 to 5.0 MHz. A portion of the solid member remote from the transducer (preferably at a distance of at least 30 wavelengths) includes at least one surface immersed in or adjacent the fluid to form a solid-fluid interface. The transducer assembly and the solid member are constructed to propagate the SV wave in the solid member along a zigzag path that is multiply-reflected at the boundaries of the solid including at least two of the reflections at the solid-fluid interface; the number of such reflections (N) in the immersed region may be as large as 100. The angle of incidence at these interface reflections is chosen to maximize attenuation of the wave by acoustic coupling to the fluid. The angle of incidence of the interrogated beam at the interface preferably exceeds the first critical angle by at least five degrees and is at least ten degrees less than the second critical angle.

The solid member is substantially homogeneous and flaw-free over the zigzag path. Depending on the beam width and the path geometry, the interrogation of the interface is either continuous or stepped, but in either case the measured fluid impedance is integrated over the interrogated surface. Electronic instrumentation that is sensitive to amplitude measures the attenuation of the beam due to the fluid coupling and thereby measures its acoustic impedance. The instrumentation may be connected to one or more separate receiving transducers or to the transmitting transducer.

In one form the solid member is an elongated buffer rod with the transducer assembly located at one end. The remote region is located generally at the opposite end of the rod. The remote region may be localized or distributed and has at least two surfaces immersed in the fluid. In another form, the solid member is a portion of a wall of a conduit or container. The interrogation is distributed and the remote region is the interior surface of the conduit or the container adjacent the fluid. The wall portion can be straight or curved and the axis of the multiply-reflected zigzag interrogation path can also be straight or curved and can have various spatial orientations. In both forms, the solid member is substantially homogeneous and flaw-free, at least along the path. Also, the surface adjacent the fluid can be coated with elastically dissimilar material such as paint or an anti-corrosion layer whose thickness is less than one-tenth of a wavelength.

While this system is designed to measure principally the impedance or level of the fluid adjacent the sensor, the measured attenuation of the interrogating SV sound wave can be affected by changes in other, non-measured variables. This invention includes system compatible arrangements using shear mode energy of the main interrogatory system to compensate for or neutralize the effects of changes in these other variables. In one form, the solid member includes a notch or other means to generate an echo along a supplemental path other than the interrogating zigzag path. The transit time of this supplemental path gives a reliable indication of the temperature of the solid member and allows electronic compensation for changes in its temperature. In another form, where the solid member is the wall of a container, a supplemental reference path in the fluid detects and compensates for changes in the temperature of the fluid, the nature of the fluid, or changes at the solid-fluid interface such as the build-up of a layer of residue or corrosion. Where the interrogating beam is generated by a transducer/wedge assembly secured to the exterior surface of the wall, the supplemental reference path is a beam of shear mode acoustic energy directed at the wedge-wall interface at a normal incidence to that interface. This normal incidence shear mode reference path yields information to compensate electronically for aging of the transducer/wedge assembly or changes in the acoustic coupling of the wedge to the container wall. In many applications, variations in the transducer or its coupling can be neutralized by having a sufficient number of reflective couplings (N) with the fluid. Preferably N should be large enough so that the product of N and the reflection loss coefficient $R_L$ exceeds 20 dB.

Spectroscopic investigation of the frequency response of the zigzag SV beam provides another supplemental reference system useful in detecting and compensating for changes in the solid-fluid interface, principally the build-up of residues. The SV beam can be transmitted as a continuous band of frequencies or as pulses, in sequence, at several discrete frequencies such as 0.5, 1 and 2 MHz. Since the residue will absorb energy selectively at the different frequencies, a comparison of the attenuation of the beam at each frequency provides a reliable determination of the presence and amount of a residue build-up.

When this invention is used to measure liquid level, the system includes features to compensate for or neutralize changes in the liquid itself which could be erroneously interpreted as changes in the liquid level. One arrangement is to orient the interrogating zigzag SV wave either obliquely or parallel to the surface of the liquid. A second zigzag interrogating path located below the liquid surface provides information on the actual impedance of the liquid. Another zigzag interrogating path located above the liquid surface provides information concerning the transducer, its coupling and losses due to the solid material.

Another liquid level measurement system according to this invention utilizes a vertically oriented, rod-like solid member or probe mounted within the container. The probe has a set of notches along one or both of its sides and a "chisel-point" tip at its end remote from the transducer and immersed in the liquid. The interrogating SV mode beam is directed axially down the sensor toward the chisel-pointed tip where it undergoes two reflections of the solid-liquid interface that yield information concerning the impedance of the liquid. The notches are structured to generate echoes of substantially equal amplitude when the probe is operated in air. However, when a notch is immersed in the liquid, and because the beam is spreading and strikes the notch before or after near-grazing incidence, there is an acoustic energy coupling between the sensor and the liquid. The resulting loss of energy to the liquid is sensed as a corresponding decrease in the echo generated by the immersed notch. Analysis of the echo amplitudes coupled with the impedance information provides an accurate and reliable indication of the liquid level. This system is particularly useful in measuring liquid level when there are two different liquids held in the container, for example, a layer of oil floating on water.

Another liquid level measuring system utilizes a portion of the container wall as the solid member. A transducer/wedge assembly coupled to the exterior of the container launches the interrogating SV wave along a generally vertical path. A set of receiving transducer/wedge assemblies are located at the reflection or "bounce" points of the zigzag wave at the exterior or air side of the container. Since the attenuation of the beam is highly dependent on the presence or absence of the liquid at the interior surface of the wall segment, a comparison of the amplitude of the received signals yields the desired liquid level measurement. In another form, the receiver assemblies are replaced by dummy reflector wedges which each return an echo to the transmitting transducer. Again, electronic analysis of the received echoes provides the desired liquid level information.

In any embodiment of this invention utilizing multiple reflections over an extended interrogating region, acoustic scatters or absorbers placed intermediate the calculated reflection points of the zigzag interrogating wave control beam spread and eliminate spurious zigzag paths.

These and other features and objects of this invention are described more fully in the following detailed description of the preferred embodiments which should be read in light of the accompanying drawings.

BRIEF DESCRIPTION OF THE DRAWINGS

FIGS. 3a–3g and FIGS. 3a'–3f' are each views in side and end elevation, respectively, of elongated rod probes for ultrasonic measuring systems constructed according to this invention;

FIG. 4 is a view in partial section of an acoustic measuring system according to this invention applied to a straight wall portion of a fluid container;

FIG. 9 is a sectional view of an ultrasonic measuring system according to this invention utilizing a pair of transducers and associated wedges which generate and receive both a zigzag interrogating signal and a supplemental reference signal that measures and compensates for changes in the transducers and their couplings;

FIG. 10 is a set of graphical representations of ultrasonic transmission pulses according to the invention using a varying interrogating frequency and spectral analysis of the transmitted pulses to provide information about the solid-fluid interface.

FIGS. 10a–d are graphical representations of broad band transmission pulses utilizing spectral analysis to measure residue at the solid-fluid interface;

FIGS. 10e–g are graphical representations of narrow band transmission pulses used in spectral analysis to compensate for residue;

FIGS. 12–14 are views in section of alternative embodiments in the invention to measure liquid impedance or liquid level in a round container together with a supplemental interrogation path through the liquid to compensate for variables such as a residue build-up or changes in the viscosity or temperature of the liquid;

DETAILED DESCRIPTION OF THE PREFERRED EMBODIMENTS

Broadly speaking, an acoustic measuring system according to this invention measures the characteristic acoustic impedance Z or a related parameter of a remote, and sometimes inaccessible, fluid, typically a liquid, by measuring the reduced amplitude of a received wave of vertically polarized shear (SV) energy. The attenuation is a response to the reflection coefficient R for this SV wave at two or more solid-liquid interfaces where the wave is reflected as it propagates along a zigzag path in a substantially homogeneous and flaw-free solid member.

Another principal feature of this invention is the fact that SV wave energy propagated in a solid and striking a solid-liquid interface, will couple strongly with the liquid if the angle of incidence, $\theta_s$ of the wave at the interface lies within certain limits. The determination of these limits involves a consideration of the energy reflection coefficient R and energy reflection loss coefficient $R_L$ at this interface.

At normal incidence the sound pressure reflection coefficient $R_p$ is given by the well-known equations $$R_p = (Z_2 - Z_1)/(Z_2 + Z_1) = (r-1)/(r+1) = \pm\sqrt{R}$$

where $Z_1$ and $Z_2$ are the acoustic impedances of the first and second media, and $r = Z_2/Z_1$. At oblique incidence the corresponding equations for longitudinal and SV shear waves become more complicated. Graphical solutions of 20 cases of oblique incidence for liquid/solid combinations are given by L. C. Lynnworth and J.N.C. Chen in Proc. Ultrasonics Symp. IEEE Cat. 75 CHO 994-4SU (1975) pp. 575–578.

Figure 1:
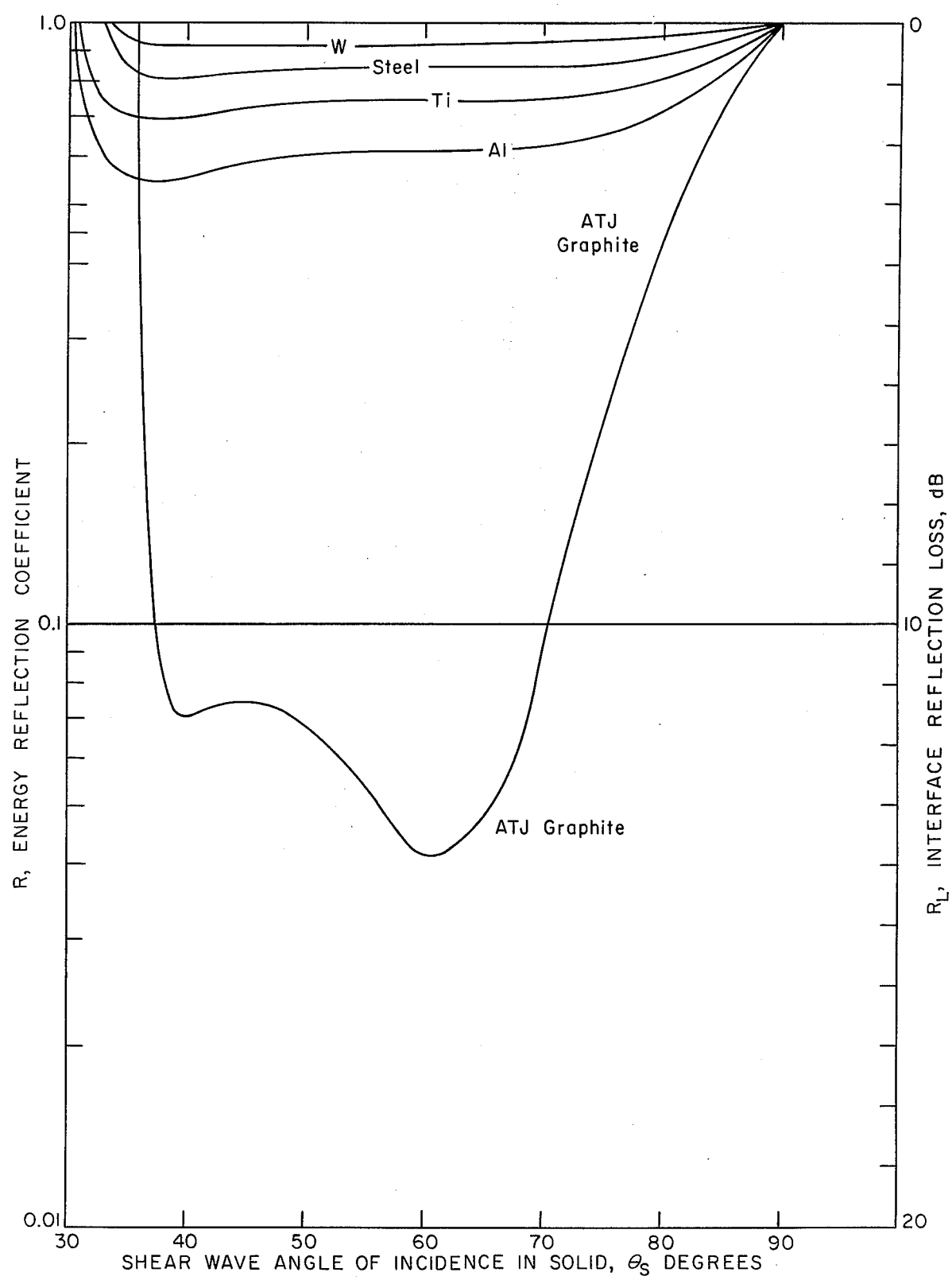
FIG. 1 is a graph and FIG. 1A is an associated schematic diagram showing the energy reflection coefficient R and the interface reflection loss $R_L$ as a function of the angle of incidence of an SV mode shear wave propagated in various solids and reflected from a water interface.

The energy reflection coefficient R for the SV energy is obtained by subtracting from unity the ratio of the SV energy transmitted to the incident SV energy. Of particular interest is the behavior of R between the first and second critical angles $\theta_{c1}$ and $\theta_{c2}$. For the purposes of this discussion these critical angles are defined as the angles where R = 1. [This definition is intended to avoid confusion with standard tables of values for the critical angles for a wave traveling in a liquid and striking a solid, while the opposite is the case here. For incidence from the liquid, the first critical angle is the angle where both the longitudinal (L) and SV waves are lost from the solid. As the angle of incidence is increased, the SV wave reappears in the solid until the angle of incidence reaches the second critical angle where it is again lost from the solid.] Between critical angles the reflection coefficient for the SV wave energy is less than 1. The angular dependence of R is shown in FIG. 1, as derived from the aforementioned Lynnworth and Chen article for the solids tungsten (W), steel, titanium (Ti), aluminum (A1) and ATJ graphite, all interfacing with water. From the log scale at the left it is seen that the minima of R range from approximately 0.914 too approximately 0.0418. The scale at the right of FIG. 1 shows corresponding values of approximately ½ and approximately 14 dB/bounce, respectively, for the reflection loss coefficient $R_L$ defined as 10 log (1/R) dB/bounce.

Figure 2A:
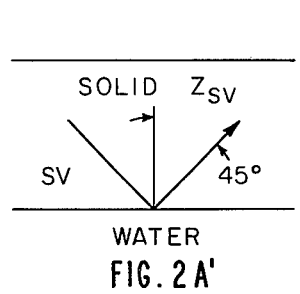
FIG. 2A is a graph and FIG. 2A' is an associated schematic diagram showing the reflection loss coefficient $R_L$ as a function of the shear wave impedance of a solid probe for a variety of solid materials at a fixed 45° angle of incidence and a water interface.
Figure 2A:
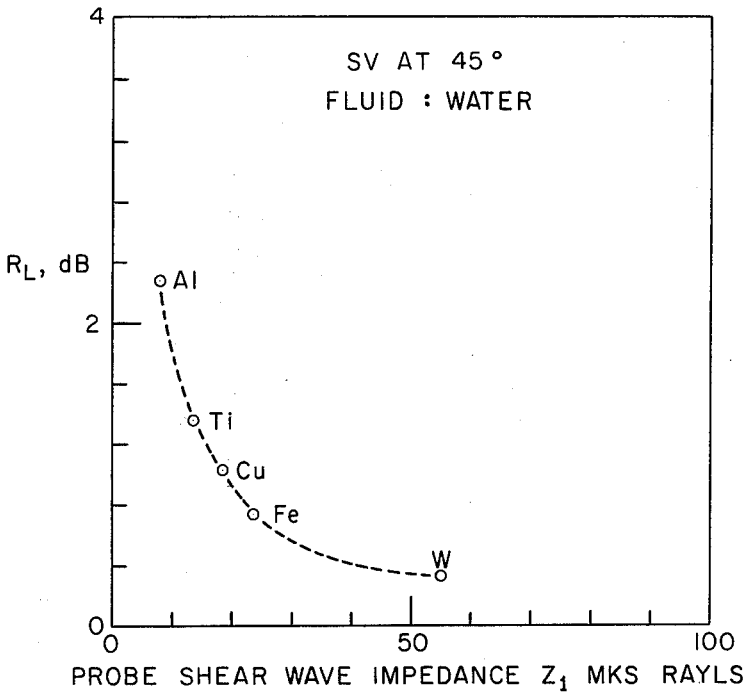

FIG. 2A, also derived from the data in the Lynnworth and Chen article, shows the dependence of $R_L$ on the SV impedance $Z_1$ of a solid in contact with water for a fixed angle of incidence in the solid, $\theta_s = 45°$. The plotted curve would shift somewhat for angles other than 45°, as is evident from FIG. 1. It is significant, however, that at any specific angle the curve is virtually insensitive to the presence of an elastic cladding that is very thin compared to the wavelength, typically less than 1/10 of a wavelength (λ). Thus the $R_L$ value can be predicted from the graph 2A even when the aluminum is anodized or the iron is nickel-plated to reduce corrosion. Similarly, a normal layer of paint will not interfere with the sound wave interaction with the solid-liquid interface. The curve is also not particularly sensitive to small variations in $Z_1$, the impedance of the solid. As a result expensive, high-purity or specially heat-treated material are not required for most applications. The small uncertainty or change in $Z_1$ due to variables in ordinary manufacturing or industrial processes will produce small or negligible error. Moreover, in many applications, such as liquid level determinations, errors due to uncertainties in $Z_1$ can be further reduced by establishing a second ultrasonic interrogation path as a reference channel in any well-known manner. (In contrast to the compensation systems of the present invention, prior art arrangements are characterized by a path completely separate from the main measuring path. The prior art arrangement typically employ transducers that transmit and receive L-mode energy.) Another way of examining the graphs in the Lynnworth and Chen article leads to the graph of FIG. 2B where $R_L$ is shown as a function of Z of the liquid (rather than the solid), using a stainless steel 304 probe and a constant angle of incidence, $\theta_s = 45°$, for the SV wave.

Figure 2B:
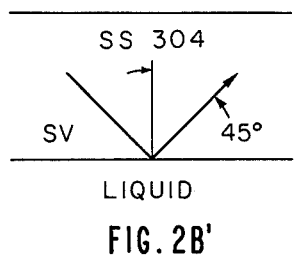
FIG. 2B is a graph and FIG. 2B' is an associated schematic diagram corresponding to FIG. 2A showing the reflection coefficient loss $R_L$ as a function of the acoustic impedance of a variety of liquids at a fixed 45° angle of incidence and a stainless steel 304 probe.
Figure 2B:
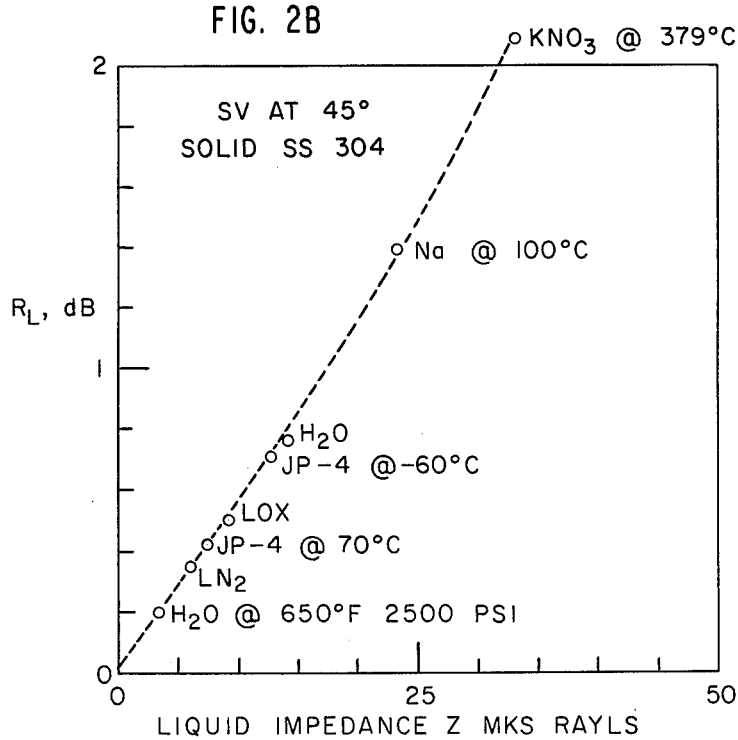

FIGS. 1, 2A and 2B and the foregoing discussion demonstrate a principal feature of this invention, that is, by using a solid of known acoustic impedance $Z_1$ and an angle of incidence $\theta_s$ in the solid that lies in a range where there is relatively strong coupling with an adjacent fluid, $R_L$ may be used as a basis for determining the acoustic impedance Z of the fluid. More specifically, as suggested by inspection of FIG. 1, the angle of incidence $\theta_s$ in the solid preferably exceeds the first critical angle $\theta_{c1}$ by five degrees and is less than the second critical angle $\theta_{c2}$ by at least ten degrees. However, it is not immediately clear that this relationship provides a measurement of Z that is sufficiently accurate or reliable. The accuracy problem stems from the fact that because the Z's vary so widely between most liquids and solids, $R_L$ is almost always small, usually less than 1 dB per bounce. Therefore, small variations in transducer coupling, or attenuation uncertainties in the solid, could easily exceed $R_L$.

The measuring system of this invention resolves this accuracy problem by reflecting the SV wave off the solid-liquid interface at least twice. This solution in turn depends on the fact that over the above specified range for $\theta_s$ (1) the SV wave can be reflected internally within the solid without mode conversion and (2) the remaining SV energy can then be controllably directed to encounter the liquid interface a sufficient number of additional times so that $NR_L$ exceeds uncertainties in attenuation due to the transducer coupling or other sources by a significant margin, where N = number of reflective interactions or "bounces". In general, $NR_L$ should exceed 20 dB. A typical value for N is 10, although values from 2 to 100 are preferred in specific applications. For an angle of incidence of 45°, it may be shown that the number of SV bounces necessary to attenuate the SV wave by 20 dB roughly equals the "acoustic contrast" $Z_1/Z$. Another advantage of this invention is the utilization of more than one interaction area to avoid errors that may be caused by nonrepresentative reflection conditions at a single area, e.g., deposits, scale or an irregular surface. The number of interaction areas will usually equal N for through-transmission interrogation mode or N/2 for a pulse-echo mode. For convenience of fabrication and path estimating, $\theta_s$ will commonly be 45° or 60°, but as shown in FIG. 1, angles from about 35° to 80° are usable for the materials illustrated.

FIGS. 3a–15d illustrate how the foregoing principles may be utilized in practical piezoelectric measurement system designs. The designs fall generally into two categories, those in FIGS. 3a–4, 11 and 14 that include a probe buffer section between a transducer and remote interaction areas of the probe, and those in FIGS. 5–8, 11–13 and 15a–15d that interrogate a portion of a container wall using external transducers to investigate internal fluid conditions. Several preferred probe configurations of the first category are shown in FIGS. 3a–3g.

FIGS. 3a, 3b and 3c each show an ultrasonic measuring system 12a, 12b and 12c, respectively that has a transducer 14 coupled to a sensor or probe 16a, 16b, 16c, respectively, in the form of an elongated rod with a generally square cross section. The transducer is located at one end of each probe and a fluid (for the purposes of this discussion, a liquid) is interrogated at the opposite end over a remote localized region, a probe tip 18a, 18b and 18c. An intermediate buffer section 20 of each probe separates the probe tip from the transducer. The buffer region preferably has a length in excess of 30 λ where λ is the wavelength of the interrogating wave. Stated more generally, the solid-fluid interface where the interactive coupling occurs should be "remote" from the transducer launching the wave, where remote is preferably in excess of 30 λ.

Each probe tip 18a, 18b, and 18c has at least two surfaces that are immersible in and capable of interacting with the liquid. In the probes 16a and 16b the tips 18a and 18b each have two interacting bevel surfaces 22a and 22b that are mutually perpendicular and oriented at a 45° angle with respect to the upper and lower faces of the probes. Probe 16c has a square cross-section tip 18c that is angled at 45° with respect to the buffer section 20.

The transducer 14 is a shear mode piezoelectric element. Typical dimensions for the transducer are a 1 to 2 cm square that is 2 MHz thick. The effective diameter of the transducer should be at least three wavelengths and preferably larger than five wavelengths. The transducer generates and transmits a shear mode SV wave that propagates axially through the probes as a moderately directional, bulk wave. To achieve this SV beam the SV wave frequency is preferably in the range of 0.5 to 5 MHz. A typical beam width is 1.25 to 2.5 cm. At higher frequencies, the scattering-induced attenuation losses in the probe become unacceptably high. At lower frequencies, beam spread becomes too great. Probes may be constructed so that, as a moderately directional unguided or bulk wave, the SV wave has little interaction with the surrounding liquid, if any, along the buffer section 20. The SV wave is reflected from the bevel surfaces of the tips 18a, 18b and 18c as shown and returned to the transducer 14 as an echo where the wave is received and detected. The tip 18a introduces two interrogating reflections (N=2). In the probe 16b, a lateral notch 23 located between the buffer section 20 and the tip 18b reflects the wave back onto the bevel surfaces so that N=4. For the probe 16c, N=6.

The attenuation of the received wave is uniquely and predominately associated with the acoustic coupling to the liquid at the bevel surface, as described above. The attenuation thus measures the acoustic impedance of the liquid. A significant advantage of this invention is that this coupling, at the frequencies indicated above, allows the measurement of liquids having a wide range of viscosities. More specifically, the invention has been found to be useful for liquids with kinematic viscosities less than ten stokes. It should be noted that the bevels are angled and oriented so that ultrasound transmitted into the adjacent liquid will not interfere with the detected echo. Also the notch 23 can provide a reference echo to initiate a receiver gate or to provide a basis for computing the impedance $Z_1$ of the probe material. For example, $Z_1$ can vary significantly where the probe undergoes wide temperature variations. Temperature variations result in corresponding variations in the travel time of the wave to the notch and/or between the notch and the remote tip. Therefore, the travel times of the echoes from the notch 23 and from the probe tip provides a measure of the probe temperature thereby providing a basis for compensating the zigzag path measurement of Z. As noted above, this compensation path, in contrast to conventional arrangements, utilizes a portion of the shear mode sound wave energy that is interrogating the fluid.

Figure 3G:
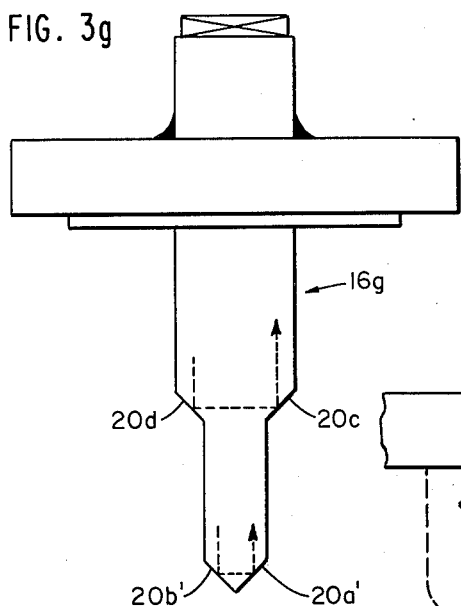
Figure 1A:
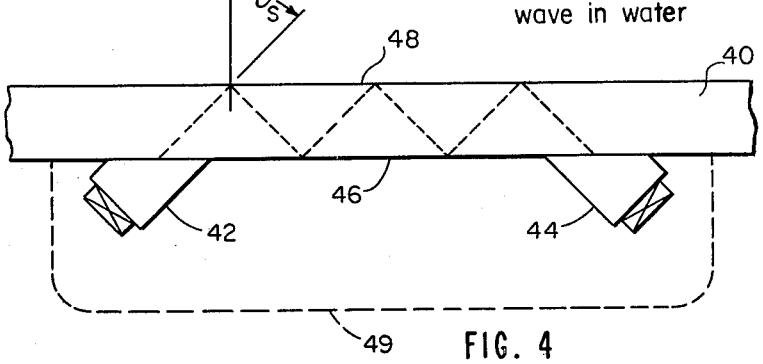

The tips 18a, 18b and 18c can be used to sense Z when the tip is fully immersed. The configuration and size of these probes make them suitable for laboratory use by insertion in a test chamber, test tube or beaker. Alternatively, they can be used to sense the presence or absence of a fluid at the vicinity of their tips. While the tips 18a, 18b and 18c are all located at the end of their associated probes, interrogating bevel surfaces can also be formed at other locations on a probe. For example, FIG. 3g shows an impedometer with a two-zone probe 16g that measures the impedance of a fluid at an end bevel defined by the surfaces 20a', 20b' and intermediate bevel surface 20c, 20d formed approximately midway along the probe. The illustrated two zone configuration also can be used to sense "high" and "low" liquid levels in a container. This general configuration can be extended to provide more than two local Z-sensing regions each remote from the transducer 14 to determine an impedance profile for the fluid.

To obtain a continuous measure of liquid level over a broader range than can be achieved with the probes 16a, 16b or 16c, elongated probes 16d, 16e, and 16f, each having a broader distribution of sensing areas, can be constructed as shown in FIGS. 3d, e and f, respectively. In the longitudinally slotted design of probe 16d, a remote probe tip 18d opposite a threaded end 16d' serves as a corner reflector. One transducer 14, mounted at a 45° incline with respect to the longitudinal axis of the probe, serves as both a transmitter and a receiver. Probe 16e uses a sealed shield 24 to prevent interaction with the liquid except over the desired remote sensing portion 25 of the probe. In the probe 16f, a 22.5° ramp 16f' reflects the axially-incident shear wave to a 45° SV zigzag wave which interacts with liquid only in the remote, thinner region 25'. Reference echoes are generated at a small notch 26 and at the probe's remote end 28. By way of illustration, the thick end of the probe can have a square cross section, 13 mm by 13 mm, and the notch 26 can have a lateral depth of 1 mm with an adjoining ramp portion 30 inclined at approximately 3°. The distributed measuring systems shown in FIGS. 3d and 3e provide N approximately equal to 10 when constructed in the proportions shown. N=20 for FIG. 3f.

Since $R_L$ is almost directly proportional to Z (as demonstrated by FIG 2b), the net attenuation over an extended sensing region, only part of which is wet by a fluid, is an integrated effect approximately proportional to the product Zh, where h is the wetted length. Separation of the variables Z and h can be accomplished using two paths, as described with reference to FIG. 5 below, or by using two probes, in a manner well known in the art.

A special liquid level determination case exists when the fluid is of known composition but at an unknown temperature T. For a known liquid, the temperature-dependence of Z can be established empirically, or calculated from available data on the temperature-dependence of density and compressibility. There remains, however, the problem of measuring T in the vicinity of the remote, distributed sensing portion 25, 25' of the sensor. One solution is to measure the travel time between reflectors 26 and 28 in the probe 16f, from which the sound speed $c_1$ in portion 25' may be calculated with reasonable accuracy. Further, T in portions 25, 25' except for transients, will usually be an accurate indicator of T in the adjacent liquid. Thus Z may be calculated and the unknown h determined from the attenuation of the SV zigzag wave in portion 25, 25'. In the event that T varies so widely that attenuation within portions 25, 25' varies significantly and independent of Z, then this internal attenuation may be determined by comparing normal incidence shear wave echo amplitudes from reflectors 26 and 28. Thus the variables Z and h may be separately determined despite the presence of interfering variables such as T and internal attenuation.

Another way to measure the temperature of the remote sensing tip involves truncating the tip. For example, consider the chisel-like tip of probes such as in FIG 3a or 3g. If the chisel's sides are orthogonal (±45° to principal axis), it is possible to truncate the tip perpendicular to the axis along a plane passing through the midpoints of the chisel sides. This shortens the chisel probe by an amount L, producing a reference echo A which precedes the doubly-reflected SV echo B by $\Delta t = t_B - t_A = 2L/c$ where c=sound speed for shear waves in the (isotropic) tip. Again, c yields T. Corner reflectors as at the end 28 of the probe of FIG. 3f could be equivalently truncated by chamfering to yield a reference echo analogous to the echo from notch 26.

Referring again to the 1979 publication by Korycki at al., it may be understood that by measuring Z and T, the pressure P of the fluid adjacent the sensing portion of the probe may be determined. Thus, P may be viewed as another impedance related parameter of the fluid.

In use, any of the designs of FIGS. 3a-3g may be installed in a conventional or modified compression fitting or in a flange 32 as shown in FIG. 3g. Conventional supports and electrical connections using square holed sleeves or similar mating shapes are also used for installation.

FIGS. 4–9 show configurations for ultrasonic systems which utilize as the solid probe member a portion of a wall of a conduit such as a pipe or a container such as a tank. In general, one or more S or L mode transducers will be coupled via external wedges to this solid wall to launch SV waves in the solid with an angle of incidence that lies within the above-mentioned range for $\theta_s$. The liquid of interest is on the inside of the solid, remote from the transducer and it is often inaccessible, as is the case for many hazardous liquids within sealed chambers. The interrogation of the liquid is distributed over one surface, the interior surface of the wall portion.

In FIG. 4 a container wall segment 40 is interrogated in zigzag fashion by SV waves at $\theta_s$ generated from an external transducer/wedge assembly 42. Signals are received by a similar assembly 44, or, to double N, the wedge portion of assembly 44 is used as a reflector, returning the interrogating wave to the transducer assembly 42 for processing and/or display by amplitude-sensing electronics. (A similar use of a dummy wedge reflector is illustrated in FIG. 8g at p. 473 of *Proc. of the Ultrasonic International Conference held in the U.K.* (1977) authored by one of the present applicants.) The transducer side 46 of segment 40 should be kept free of variable external surface conditions such as rain, wet paint, biological residue or deposits. A cover 49 may be installed for this purpose. There, however, may be no opportunity to control the condition of remote surface 48. If possible, this problem can be controlled by first ultrasonically scanning a region of interest using conventional L-mode normal incidence reflectometry equipment such as a pulse-echo flaw detector. Locations are preferred where surfaces 46 and 48 are substantially parallel or concentric, and where the segment 40 is substantially homogeneous, flaw-free and weld-free. If the assemblies 42 and 44 are to be permanently bonded to the surface 46, then some routine surface preparation is recommended. This preparation may consist merely of cleaning with a solvent, but may include abrasive procedures to generate flat, paint-free, and rust-free areas.

In some applications, it is important to maintain the "external" surface, i.e. the transducer side 46, of the wall segment 40, at a constant temperature. One way to achieve this temperature stability is to immerse the external surface of the container in a liquid. To minimize errors due to interpretation of the wave amplitude that propagates between surfaces 46 and 48, the external surface should be immersed in a nonvariable manner, e.g., water at constant depth and constant temperature (constant impedance). If the fluid adjacent the external surface has an impedance $Z_e$, and the fluid adjacent internal surface has a different impedance $Z_i$, the attenuation along the zigzag path at a particular angle $\theta_s$ will depend on (1) the ratios $Z_e/Z_{40}$ and $Z_i/Z_{40}$, where $Z_{40}$ is the impedance of the wall segment 40, and (2) the number of wetted bounces. The attenuation will include the sum of the losses at surfaces 46 and 48. For the conditions of FIG. 2B, $R_L$ is nearly proportional to Z for Z up to at least 25 mks rayls ($R_L \cong 0.06Z$ dB·bounce$^{-1}$·rayl$^{-1}$). Therefore, for a known $Z_e$, and a known container path segment 40, the attenuation due to $Z_i$ is calculable. Alternatively, if the container can be emptied (so $Z_i=0$) and then immersed in $Z_e$, the "external" contribution to attenuation can be determined. If $Z_e$ is variable then a supplemental reference path may be required as discussed below in connection with FIG. 5.

Figure 5:
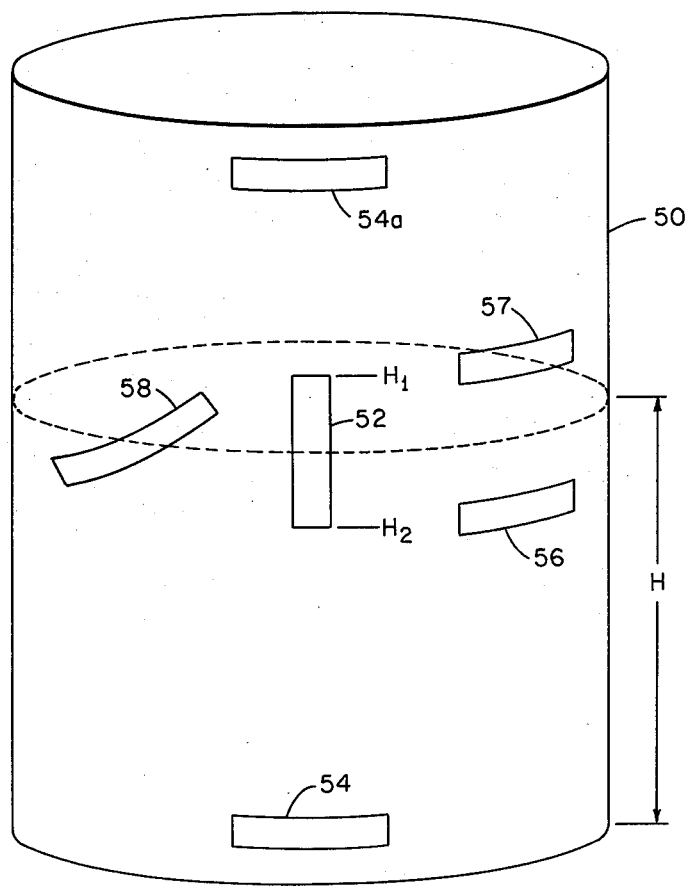
FIG. 5 is a schematic view in perspective showing various arrangements for measuring liquid level in a curved wall tank utilizing one or more ultrasonic systems according to this invention.

FIG. 5 shows various SV zigzag interrogation path locations and orientations that may be used on a container such as cylindrical tank 50, in which the remote liquid level H is to be determined using transducer assemblies attached externally. Vertical path 52 provides for continuous measurement of level with its range $H_1$ to $H_2$. Since the attenuation is an integrated effect of Z over that part of the path h which the liquid wets, it may be necessary to compensate for changes in the impedance Z of a considerable magnitude by utilizing a reference path 54 which includes the same number of internal reflections at $\theta_s$ as does the vertical path 52. Path 54 is positioned low enough so that it is fully immersed on the tank's remote side. Measurement of the total attenuation in path 54 yields Z; comparison of losses over paths 52 and 54 yields h; and knowledge of the path position (height) yields liquid level H. Alternate reference path 54a located above the maximum liquid level provides an unwetted path from which losses due to transducers, coupling, beam spread, and the like, all independent of the liquid, may be ascertained.

For extremely high sensitivity to specific levels $H_1$ and $H_2$, horizontal paths 56 and 57 may be utilized. By arranging for $NR_L$ to exceed 20 dB when such paths are wetted, level control can be achieved with electronics that is tolerant of spurious amplitude changes due, for example, to variations in coupling or transducer aging.

The horizontal path also tends to immunize the system against relatively large changes in the impedance Z of the liquid to be sensed inside the tank. To understand this immunity to Z variations, refer again to FIG. 2B, or to the corresponding approximation, $R_L \cong 0.06$ Z. Suppose Z varies from 10 to 20 mks rayls. Then $R_L$ would vary from 0.6 to 1.2 dB/bounce. If N=16 bounces are utilized, then $NR_L$ would vary from about 10 to 20 dB. If a reference voltage level is established corresponding to a dry inside (Z=0), one can calculate that if the inside surface is then wetted by a liquid whose impedance Z is 10 to 20 mks rayls, then the received signal will be attenuated by an additional 10 to 20 dB. With a threshold set at 9 dB below the "dry" reference voltage, a comparator and peak detector can detect when the level has risen to intersect the horizontal path, since, for Z between 10 and 20 mks rayls, the attenuation will increase by more than 9 dB, i.e., by 10 to 20 dB.

To achieve intermediate sensitivity, an oblique path 58 may be utilized. Sensitivity of various orientations may be defined by the ratio $NR_L/\Delta H$ where $\Delta H$ equals the level difference over which the zigzag wave is attenuated by $NR_L$ dB. By way of example, $NR_L/\Delta H$ can range from approximately 20 dB/cm to approximately 20 dB/m. It should be recognized, however, that the increased sensitivity of the oblique path makes this measuring system more sensitive to variations in other variables such as changes in the nature of the liquid in the container, changes in temperature, and the other spurious factors influencing the measured attenuation mentioned above. One or more supplemental reference paths such as paths 54 and 54a are therefore recommended for many applications.

Figure 6:
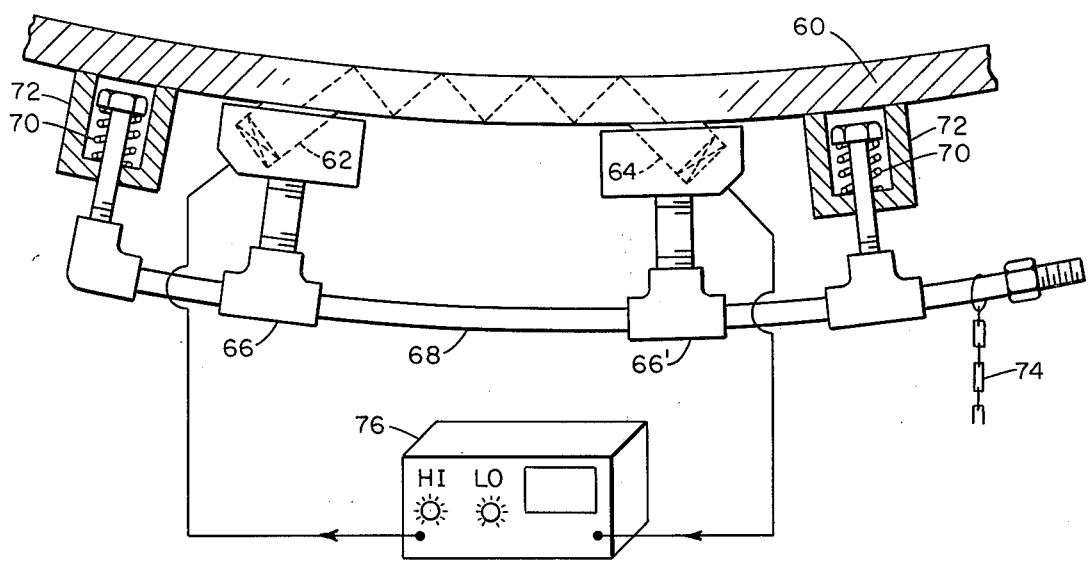
FIG. 6 is a top plan view partially in section of an arrangement for mounting the systems shown in FIG. 5.

FIG. 6 represents an externally-mounted ultrasonic measuring system according to this invention attached to a steel (magnetic) tank wall segment 60. Transducer assemblies 62 and 64 are initially adjusted to optimum positions as described above. Drilled-through compression fitting tees 66, 66' are tightened against the support rod 68. This rod applies pressure by virtue of the springs 70 captured within the cylindrical horseshoe magnets 72, 72. Pressure may be applied to the transducer assemblies through straight rods or through swivels. For permanent bonding, the assemblies 62 and 64 may be epoxied to the external surface of segment 60. Since epoxies may be mixed with adjustable cure times, a suitable formulation may be selected which remains fluid for enough time to optimize the positions of transducer assemblies, yet cures to adequate strength after the proper locations have been identified. After curing, the "scaffolding" may be removed. In some cases it will be desirable to retain a mechanical restraint such as a chain 74, as a safety measure to assure that the assemblies cannot fall and injure workers underneath the measuring site.

An electronic console 76 is a pulser/receiver with amplitude-responsive signal output or display, preferably Panametrics' model LLX which transmits cw, rf bursts or broadband pulses at selectable center frequencies such as 0.5, 1, 2 or 5 MHz of adjustable duration, and which contains a gateable receiver. The amplitude of the transmitted wave may be electronically controlled to yield a preset amplitude level at the receiver transducer, e.g., 10 mV. The dc voltage V which controls the transmitted amplitude is thus a measure of attenuation over the zigzag path. V may be measured directly or after logarithmic amplification which converts attenuation in dB to a level reading H in conventional units (mm) or to an acoustic impedance reading Z in rayls. Alternatively V may be compared with preset voltage levels corresponding to limits on Z or on H. The model LLX incorporates a two-gate receiver to compare received signals after propagation over different paths, and a hysteresis comparator to minimize chatter due to sloshing when H is to be measured. This instrument also provides relay closures corresponding to preset V levels being reached. While the console 76 is shown in use with a distributed mode measuring system using a container wall as the solid member, it will be understood that it is also used to generate and process signals in the other embodiments described herein.

Figures 7, 7A:
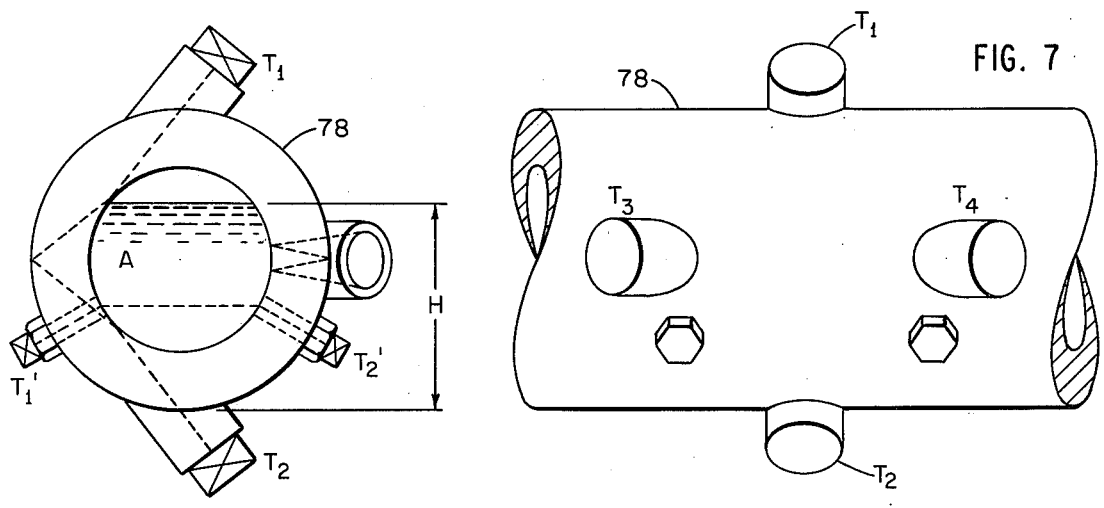
FIG. 7 is a view in side and FIG. 7A in end elevations of an ultrasonic measuring system according to this invention applied to a conduit partially filled with the fluid and used to measure its mass flow rate.

FIGS. 7 and 7A shows the application of this invention to measuring the level H of a liquid in a partly-filled pipe 78. The transducer assemblies $T_1$, $T_2$ are coupled to the top and bottom of the pipe. Although the zigzag wave is shown as bouncing twice, it usually bounces many times before traversing the semicircumference (defining a path analogous to "vertical" path 52 in FIG. 5). Conventional flow velocity sensing transducers $T_1'$, $T_2'$, operating independently of the assemblies $T_1$ and $T_2$, are also coupled to the pipe 78. The volumetric flow rate Q is determined from this configuration based on the product VA, the liquid cross sectional area A being calculated from H. A second pair of impedance measuring transducers $T_3$, $T_4$ provides a value for Z which can be used to refine the H measurement to be used in computing mass flow rate $\dot{M}$.

Figure 8:
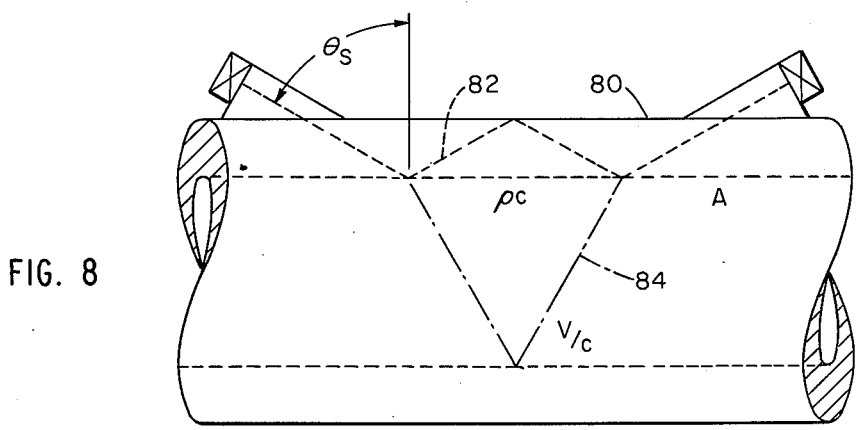
FIG. 8 is a view in side elevation of an alternative arrangement for measuring the mass flow rate of a fluid in a conduit.

FIG. 8 shows an ultrasonic measuring system according to this invention applied to a full pipe such as a water-filled steel pipe 80. Zigzag path 82 senses Z which equals the product of the density of the liquid in the pipe and the velocity of sound in the liquid. Path 84 in the liquid can be interrogated in upstream and downstream directions to obtain the Mach number V/c from the ratio of time difference to time sum. The travel times along these two paths 82 and 84 are usually quite different. A dual-gate receiver is used to distinguish propagation over each path. For example, if the pipe diameter is 1 m, if $\theta_s=60°$, and if $c_l$ in the pipe=3000 m/s and c in the liquid=1500 m/s, the travel time along path 82 will be about 400 microseconds while that along path 84 will be about 1500 microseconds. The product of (pc) and (V/c) is proportional to $\dot{M}$, the mass flow rate.

FIG. 9 shows another embodiment of the invention similar to the embodiments shown in FIGS. 5 and 6 in that the interrogating zigzag wave is propagated in a segment 92 of a container wall and is generated by transducer/wedge assemblies 100, 100a secured to the outer surface of the container. The distinctive feature of this embodiment is a supplemental reference path that is responsive to the coupling at the wedge/wall interface, transducer aging, and debonding of the transducer from the wedge. A transducer 91, bonded to wedge 90 which is in turn coupled to the wall segment 92, launches an incident wave 97 that strikes a chamfered surface 90a to reflect an SV shear wave 98 obliquely into the wall segment 92 through the wedge-wall interface 92a. At the same time another portion 99 of the incident wave 97, derived from the same transducer 91, also encounters the interface 92a of the wedge and the wall segment. By coupling without a fluid couplant at interfaces 92a, 92b, the normal and oblique reflection and transmission coefficients of the waves 99 and 97, respectively, can be made to remain in approximately constant ratios. Thus, the amplitude of received signal 96 in a wedge 90b of the assembly 100a, being obliquely transmitted at interfaces 92a, 92b, is attenuated in approximately the same proportion as a reference echo 94 of the wave 99, provided conditions at the interfaces 92a and 92b are similar. To avoid the need for similar conditions at these interfaces, one can alternately transmit at assembly 100 (receiving at 100a) and then transmit at 100a (receiving at 100). The reference echo 94, and its counterpart 94a in wedge 90b, would be added or averaged, and serve as a basis for comparison to the received signal 96. If reverberations in the wedges 90, 90b decay prior to the reception of zigzag wave 95, it is possible to drive both transducers 91, 91a in parallel while receiving separately (using conventional diode isolators or equivalent switching circuits). This facilitates the addition of signals generated in the transducers by the reference echoes 94, 94a as well as the received signal 96 and its contrapropagating counterpart (not shown). The sums may then be compared and interpreted to yield, with a high degree of reliability, the attenuation attributable to fluids adjacent the segment 92 without serious error due to coupling variations at either interface 92a or 92b.

It should be noted that the incident wave 99 generates a reference echo 93 at the wedge-segment interface 92a as well as the reference echo 94 at the solid-fluid interface. The echo 93 may be used to establish a time gate or window for measurement of the echo 94, and/or the echo 93 may be used itself as a measure of the reflection coefficient at interface 92a. The echo 93 provides information about the interface 92a because the incident energy is equal to the reflected energy in the echo 93 plus the energy transmitted into the wall segment 92. It should be noted that this shear mode supplemental path differs from "longitudinal" checks on the degree of coupling of angle probes as shown, for example, in the above referenced book by Krautkramer at p. 297.

FIG. 10 relates to a further feature of this invention where the zigzag interrogating wave is varied in frequency. Analysis of the resulting ultrasonic spectrum provides information about the condition of the solid-fluid interface. This feature is particularly important in applications where a liquid leaves a deposit or residue on the solid member. These residues can attenuate the interrogating waves causing errors in the impedance or liquid level reading. Periodic cleanings of these residues are one solution to the problem, but cleaning is not often practical or possible. In these circumstances, spectral analysis provides information on the presence and thickness of the residue. For example, a clean wetted interface should yield $R_L$ independent of frequency; residues may increase the apparent $R_L$ at high frequency or at molecular relaxation frequencies.

FIGS. 10a–10d illustrate spectral analysis with a broad band transmission pulse generated by a ultrasonic system of the type shown in FIG. 9. FIG. 10a and 10b illustrate the characteristics of the reference echo 94 in both the time domain and the frequency domain, respectively. In the time domain, the reference echo has, for example, a pulse width of 100 nanoseconds. The reference echo in the frequency domain has a broad frequency spectrum with the envelope peaking for example, near 5 MHz. In contrast, if the interrogating pulse 95 traversing the zigzag path in the container wall segment 92 encounters a sticky residue at the solid-liquid interface, the high frequency components of the pulse are selectively attenuated. The received signal 96 would appear generally as shown in FIGS. 10c and 10d. In the time domain, the received signal would appear "smeared" with a broadened pulse width of perhaps 300 nanoseconds. In the frequency domain, the envelope of the received spectrum will peak at a comparatively low frequency, for example, 3 MHz.

It is also possible to interrogate with stepped or swept frequency rf bursts having a narrow band centered sequentially on frequencies such as 0.5, 1, 2, and 5 MHz (FIGS. 10e–10g). Suitable electronic equipment for generating transmission pulses at discrete or continuously swept frequencies is commercially available (as for example the Panametrics' model LLX described above) or can be assembled from standard commercial equipment as described in *Ultrasonics*, 17 (4) pp. 183–185 (July, 1979) by P. M. Gammell.

It should be noted that the zigzag path of a moderately directional, bulk SV wave traversing a zigzag path in accordance with this invention will exhibit some minor frequency dependence even in the absence of a sticky residue coating at the solid-liquid interface. These losses, due to the competing effects of beam spread, grain scatter, and absorption in the probe or container wall, however, can be determined by calibration. Losses in excess of these can then be ascribed to the residue build-up.

It should also be noted that occasionally the residue is not a sticky layer at the solid-liquid interface, but rather a powder which precipitates above the liquid level. While the powder does not attenuate the interrogating wave, it can cause errors in the readings because it prevents the solid from being wetted by the liquid. To some extent, the effects of such powder deposits can be controlled by shields the type shown in FIG. 3e. The shielded region may be quite long and include most of the length of the probe. For example, the probe of FIG. 3a can be shielded almost to the remote chamfered tip 18a. In the embodiment shown in FIG. 3f the shield could protect the probe portion from the transducer to the chamfer surface 16f. In either case, the shield can readily extend for distances equivalent to 100 λ where λ is equal to the shear wavelength in the probe. In the absence of a shield, powdery deposits can be removed or prevented by vibrating the probe vigorously, spraying it periodically with a cleansing jet, or heating it.

Figures 11, 11A:
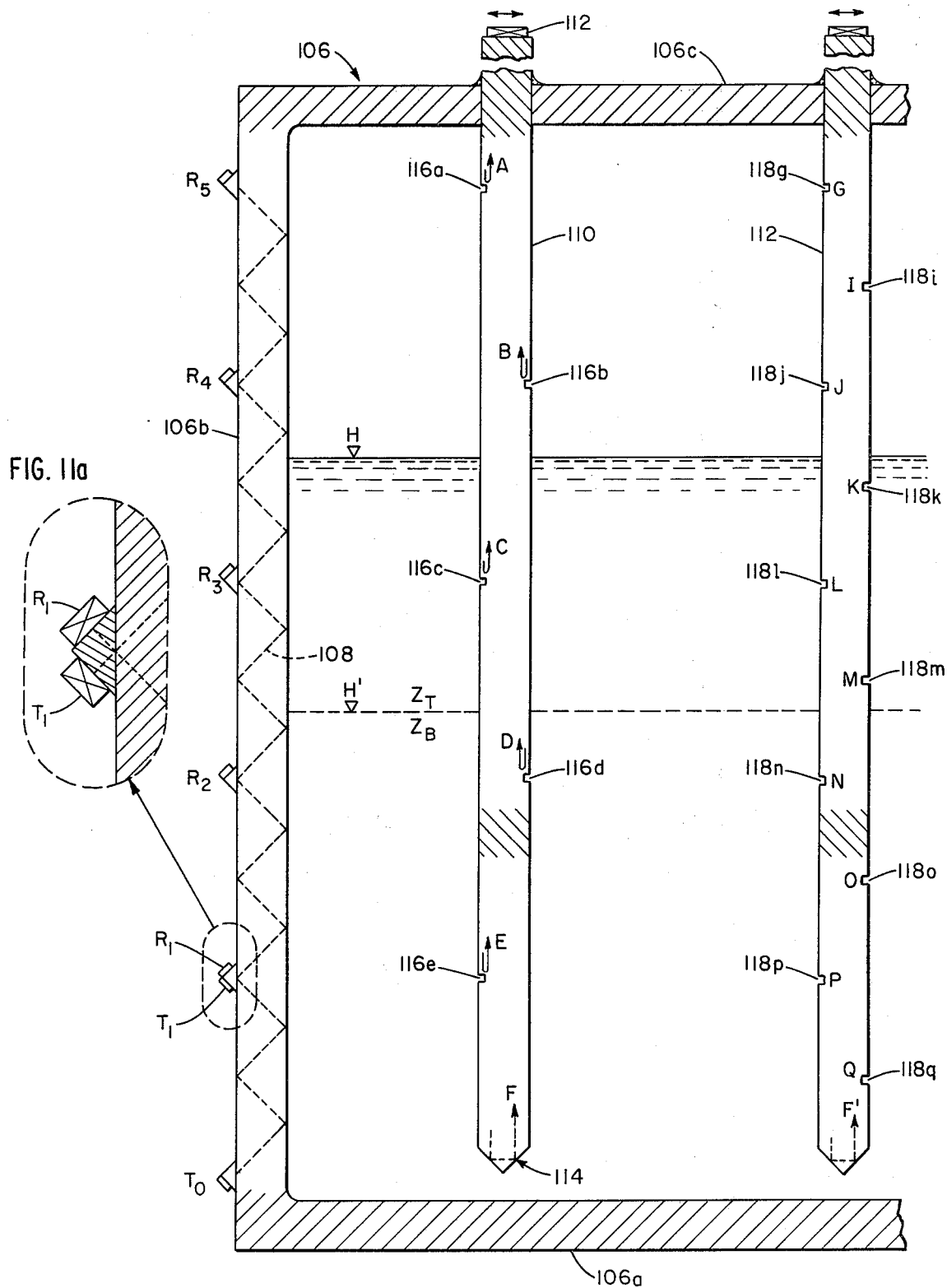
FIG. 11 is a view in cross-section of a container with various arrangements according to this invention for measuring liquid level in the container including the levels of two dissimilar liquids.
FIG. 11a is a detail view showing the transducers T1 and R1 of FIG. 11 attached to a common wedge.

FIG. 11 shows several other embodiments of the present invention where, as in the FIG. 5 embodiment, moderately directional, bulk SV mode energy propagated along a zigzag path in a solid member is used to determine liquid level in a container. The embodiments shown in FIG. 11 are particularly useful in detecting liquid level where there are two or more types of liquid held in the container (e.g. an oil and water combination) and it is desirable to locate both the uppermost liquid level as well as the interface between the two liquids. A major advantage of these ultrasonic measuring systems is that they are substantially insensitive to or can compensate for changes in the acoustic impedance of the liquids and therefore are capable of providing reliable information concerning the liquid level.

In FIG. 11, a tank 106 holds a first liquid, for example, water, having an acoustic impedance $Z_B$ that fills the tank from its bottom wall 106a to a level H' and a second liquid, for example, oil, having an acoustic impedance $Z_T$ which extends from the level H' to a level H. Air and/or other gases fill the space in the tank 106 above the level H. In a first embodiment of the invention, the side wall 106b of the tank acts as the solid member which propagates SV mode acoustic energy along a zigzag path 108. As shown, the axis of the path 108 is substantially vertical. A set of transducer/wedge assemblies $T_0$, $R_1$, $R_2$, ... $R_5$ are acoustically coupled to the outer surface of the wall 106b. The lowermost transducer assembly $T_0$ is a transmitter for the SV zigzag wave and the assemblies $R_1$, $R_2$ ... $R_5$ are receivers. The acoustic coupling of each assembly to the wall 106b is as uniform as is possible.

The receiver assemblies $R_i$ are each located at a point where the interrogating wave will reflect or "bounce" at the outer surface of the wall 106b. The precise location of the receiver assemblies will therefore depend on the angular orientation of the transmitter assembly $T_0$ with some consideration being given to other factors such as the degree of beam spread. Attenuation of the transmitted wave 108 will be due to normal attenuation within the solid member and the attenuation due to the coupling at the solid-liquid interface as described above in connection with FIGS. 1 and 2. The presence of a liquid in the tank will attenuate the beam 108 more than if there is no liquid present. As a result, the received signals at the wedges $R_1$–$R_5$ yield the liquid level H.

Further, if $Z_B$ is sufficiently different from $Z_T$, the difference in received signals at the various receiver wedges $R_i$ can also be interpreted to yield the interface level H'. Several steps can be taken to increase the reliability of the measurement of H'. One is to attach transmitter transducers to the receiver transducer wedges $R_i$ as shown in detail in FIG. 11a where a transmitter transducer $T_1$ secured to the same wedge as the receiver transducer $R_1$. The transmitter transducer $T_1$ is oriented to launch an SV mode wave of the same character as the one launched by the transducer $T_0$ and along the same path. A comparison of the transmission between the transmitters $T_0$ and $T_1$ and each of the receiving transducers provides information which yields the desired interface level H'. A second step to enhance resolution is to orient the entire transmission path 108 so that it is oblique rather than vertical, in a manner similar to the path 58 shown in FIG. 5.

FIG. 11 also illustrates the use of areas 109 intermediate ziz-zag bounce points that dissipate acoustic energy by scattering or absorption. This feature is applicable to most embodiments of this invention, but particularly those where there are a significant number of reflections (operation in a distributed mode). For scattering, the area 109 can be a roughened or uneven portion of the unwetted surface of the solid member, in this instance the container wall 106b. For absorption, the region 106b can be a strip of an adhesive tape that is secured to the outer surface of the wall 106b. In either case, the attenuative regions on selected surface areas of member 106b should substantially dissipate any acoustic energy that strikes it. This dissipation controls beam spread and ensures that only zig-zag waves that have undergone a preselected number of reflections along a predetermined path will be sensed at the receiving transducer. This in turn avoids ambiguity in the received signal and incorrect readings.

FIG. 11 also illustrates another embodiment of the invention utilizing an elongated probe 110 which extends vertically into the tank, secured at its upper end in the top wall 106c of the tank. The probe 110 is generally similar in its geometry and operation to the measuring system shown in FIG. 3a. A transducer 112 located at the upper end of the probe 110 vibrates in the shear mode and launches an acoustic energy beam that is polarized to provide SV mode energy at a doubly chamfered tip 114 of the probe 110. Due to normal beam spread, as the interrogating wave proceeds axially down the probe 110, the wave strikes the side walls of the probe 110 at an angle $\theta_2$ which will typically be near the second critical angle. At the tip 114, the SV wave will undergo two reflections (N=2) and couple with the surrounding liquid to provide information concerning its impedance.

The side walls of the probe 110 have small notches 116a . . . 116e which are structured to generate reflected echoes A, B, C, D, and E, respectively. The notches are also structured so that (1) they reflect only a small percentage of the energy incident on them and (2) they produce echoes, when the probe 110 is operated in a vacuum or air, that are of equal amplitude. While the notches 116 are shown as being substantially rectangular and on both sides of the probe 110, it will be understood that they can assume a variety of configurations and can be situated on only one side of the probe. An additional design consideration is that the notches should minimize errors due to reverberation between the notches. That means the sound pressure reflection coefficient should be kept small, generally less than 0.2, and preferably less than 0.1. This design criterion is particularly important if the notches are spaced equidistantly.

In operation, when the probe 110 is partly immersed in a liquid, a rough measure of liquid level is immediately obtaining by comparing the relative heights of the echoes A, B, . . . E, since a diminution in the size of the echo means that the associated notch is immersed in the liquid. This information can be used, for example, as a remote multi-level switch. Further, a comparison of the echo E and the signal F returned from the tip 114 provides information that yields the impedance of the lower liquid in the region of the double chamfer. Still further, as with the embodiment utilizing multiple receiver wedges, if $Z_T$ and $Z_B$, the acoustic impedances of the two liquids held in the tank 106, are sufficiently dissimilar, comparison of the echoes generated by the notches 116a . . . 116e can be interpreted to yield a location of the interface H'. To obtain a more accurate measure of H', the notches 116 can be increased a number and moved closer together. However, reverberations between the notches provide an effective limit on the closeness of the spacing. To resolve this problem, this invention comtemplates a second or additional probes 112 similar in construction and operation to the probe 110 with notches 118g . . . 118q which generate echoes G, I, J, . . . Q. The number, location and spacing of the notches is chosen to yield the desired degree of certainty as to the level of H and H'.

The probe 110, alone or with probe 112, can also be used in another manner where only one liquid is present in the tank but it is desired to measure its impedance gradient. Rather than the amplitude of an echo generated at the notches, the measured quantity is the transit time (and therefore the speed of sound) from the transducer to a given notch and back to the transducer. This general method of operation is discussed in U.S. Pat. No. 3,636,754 to Lynnworth, Patch, and Carnevale and is analogous to the action of the notch 26 on the probe of FIG. 3f. When the probes 110 and 112 are operated in this manner, the signal F or F' generated at the double chamfered tip measures the liquid impedance $Z_B$ at the bottom of the probe. The information concerning the transit time to the various notches provides a temperature profile along the length of the probe. For a liquid whose impedance is a known function of temperature, it is then possible to combine this information to yield the desired impedance gradient or profile. (See also, a subsequent discussion of FIGS. 15a–15b wherein notch echo amplitudes are analyzed to interpolate level and/or interface position.)

FIGS. 12–14 show still further embodiments of the invention each characterized by a supplemental interrogating path through the liquid whose impedance or level is being measured. A principal advantage of these embodiments is that the in-liquid, supplemental interrogation path insures that the attenuation of the zigzag wave in the solid member is responsive to the impedance and/or level of the liquid, not to a residue buildup at the solid-liquid interface. Another significant advantage of these embodiments is that they provide a way of utilizing the ultrasonic measuring techniques of the present invention on tanks, pipes or the like (1) near the path extremities and (2) despite the presence of obstacles on the exterior of the containers such as couplings, inlet pipes, instruments or other interruptions in the principal zigzag interrogating path. In each of these embodiments, the in-liquid supplementary interrogation path should travel a significant distance in the liquid, which for the purposes of this application can be defined as at least twice the thickness of any residue layer.

Turning now to the specific embodiments, FIG. 12 shows the liquid path concept as applied to a container or conduit 120 that contains a liquid whose level lies between $H_1$ and $H_2$. The liquid is interrogated by a pair of transducer/wedge assemblies 121 and 121a that generate and receive an angled SV mode beam of the type described hereinabove. The transducer 121 launches a wave 122 propagated in a generally axial or longitudinal direction 124 in the portion of the wall of the container 120 adjacent and below the transducer 121. At each interactive reflection or bounce point 122a, a portion of the incident energy is transmitted into the liquid and traverses the liquid along one of the paths 123a, 123b, or 123c (provided, that the bounce point is wetted by the liquid). While three in-liquid paths are shown in FIG. 12, the number of such paths will vary depending on the given application and the liquid level. Path 125 is a graphic representation of a typical path followed by the interrogating beam launched by the transducer 121 and received at the transducer 121a. For each path 123, and the representative path 125, where the speed of sound in the container or pipe 120 is given by $c_1$ and the speed of sound in the liquid is given by $c_2$, the length of the in-liquid path $L_s$ is equal to $D/\cos \theta_2$ or $$D/\cos [\sin^{-1}[(c_2/c_1) \sin \theta_1]]$$

where $\theta_1$ is the angle between the path 122 and a normal to the solid-liquid interface, $\theta_2$ is the angle between the in-liquid path and a normal to the solid-liquid interface, and D is the diameter of the container 120.

In operation, the time required for any interrogating wave launched by the transducer 121 to reach the transducer 121a will be the same provided that the signal proceeds alone one of the in-liquid paths 123a, 123b, or 123c, i.e. in-liquid the path portion emanates from a wetted bounce and is received at a wetted portion of the container 120. If one or more of the potential wetted bounce points 122a are in fact not wetted because the liquid level has not reached that point, then transmission along the associated in-liquid path will not take place. As a result, the signal received at the transducer 121a is increased in strength as the liquid level rises from the level $H_1$ to the level $H_2$. This increase in signal strength can be interpreted reliably as an indication of the liquid level within the container 120. It should be noted that this ultrasonic measuring system for liquid level relies on amplification of the received signal. In other embodiments (for example the path 52 described with reference to FIG. 5 or the path 122 below the transducer 121 that does not include an in-liquid portion), the level or impedance of the liquid is measured by an attenuation of the received signal. It should also be noted that the embodiment described with reference to FIG. 12 works properly as long as the acoustic energy is transmitted along the paths as described above. In particular, circumferential paths through the wall of the container (with no in-liquid path segment) would cause ambiguity in the interpretation of the received signal.

FIG. 13 shows an alternative arrangement for using an in-liquid path as a supplemental reference device. In this instance, however, the invention is used to measure the liquid level in a container or conduit 130 which is oriented horizontally and a principal zigzag interrogating path 132 in the wall of the pipe is circumferential. The beam traversing the path 132 is launched by a transducer 134 secured on an angle beam transducer/wedge assembly 135 which in turn is coupled to the exterior surface of the container 130 at approximately its vertical midpoint. A transducer 136 associated with an angle beam transducer/wedge assembly 137, also coupled to the exterior surface of the conduit 130 but at a point diametrically opposed to the wedge assembly 135, receives the interrogating beam 132. The transducers 134 and 136 form an angle $\theta_1$ with respect to a normal to the first internal bounce point 132a. As in the FIG. 12 embodiment, if the bounce point 132a (or succesive internal bounce points) are wetted by the liquid held or carried in the container 130, a significant portion of the beam energy will be transmitted in the liquid along a chordal path 133a which forms an angle $\theta_2$ with the normal to the associated bounce point. If the point where the chord 133a strikes the interior of the pipe 130 near the transducer/wedge assembly 137 is also wetted, that signal will be transmitted to the solid pipe wall and transmitted along a zigzag path to the transducer 136. Assuming that the liquid in the container 130 is at a level $H_2$ which nearly fills the container, the chordal, in-liquid path 133a will emanate from and be received at wetted portions of the solid container wall. The length of the chordal in-liquid path is equal to $D \cos \theta_2$ or $$L_s = D \cos [\sin^{-1}[(c_2/c_1) \sin \theta_1]]$$

where D is the inside diameter of the container 130, $c_1$ is the speed of sound in the wall of the container 130 and $c_2$ is the speed of sound in the liquid.

In the FIG. 13 embodiment, as in the FIG. 12 embodiment, there is a possibility for confusion in the received signal unless the wall/borne signal arrives at a time distinct from that of the liquid-borne signal. Since $c_1$ is usually approximately twice $c_2$, ordinarily it is easy to distinguish between these signals. It should be noted that subsequent wetted bounces of the wave beam 132 at bounce points 132b and 132c generate in-liquid chordal paths 133b, 133c– *These additional chords have substantially equal lengths and are part of acoustic paths between the transducers 134 and 136 which have substantially equal time delays, provided, of course, that the radiating and receiving points of the chords are at wetted portions of the interior surface of the container 130.*

The operation of this liquid level ultrasonic measuring system is essentially the same as that described with reference to FIG. 12. A higher liquid level will result in additional in-liquid paths and a corresponding amplification in the signal received at the transducer 136. This amplification can be interpreted as a liquid level reading. It should be noted, however, that for certain high levels the chordal paths will not be received at a fixed receiver transducer such as transducer 136 in the illustrated embodiment. This situation is graphically represented by chord 133d in FIG. 13.

To detect liquid levels below the midpoint of the pipe 130, the transducer/wedge assemblies 135 and 137 each include a second transducer 134a and 136a, respectively, which operate in the same manner as the transducers 134 and 136 except that they interrogate the lower half of the container 130 rather than the upper half. This system is useful, for example, to measure a liquid level such as that shown as $H_1$ in FIG. 13.

In contrast to FIGS. 12 and 13 where the zigzag interrogating beam according to this invention is carried in a wall portion of a container or conduit, FIG. 14 shows an embodiment utilizing the same principles where the interrogating beams are carried in a pair of elongated probes 140a and 140b that are disposed in a parallel, spaced relationship with respect to one another. A transducer 142a launches a shear mode interrogating beam which is propagated along a zigzag path 144 in the probe 140a with a transmission speed $c_1$. A transducer 142b secured at the corresponding end of the probe 140b transmits and receives a shear mode beam along a zigzag path 146. The probe 140b is adapted to receive acoustic energy transmitted through a liquid between the probes and travelling along a supplemental in-liquid path 143a. A typical sound transmission path for an interrogating beam is indicated by the reference numeral 143 in FIG. 14. As shown there, the beam will follow the path 144 for a certain number of bounces in the probe 140a, traverse an in-liquid path portion to the probe 140b where it propagates to the bottom of the probe 140b and is reflected upwardly along a zig-zag path 146a to the transducer 142b. The operating principles of this embodiment correspond to those described above with references to FIGS. 12 and 13. Increases in the amplitude of the signal received at the transducer 142b are proportional to the liquid level H. The in-liquid beam 143a, is shown as having a beam width or wave front 141 that is at least equal to the width of the transducer 142a that launched it. As a result, the received energy following the zigzag path 146a in probe 140b does not need to coincide with an "ideal" zigzag path in the probe 140b centered on the radiation pattern of the transducer 142b and indicated by the path 146.

In these FIGS. 12-14 embodiments a variation in the interrogating frequency can be useful to distinguish between wall-borne and liquid-borne beams. For example, if the wall material is a coarse-grained metal such as stainless steel 316, and the liquid has a low attenuation coefficient (e.g. water), then it is possible to interrogate the "liquid" path with a beam at a high frequency (e.g. 5 MHz) and interrogate the wall path at a relatively low frequency (e.g. 0.5 MHz).

With these embodiments, the increase in the signal level corresponding to the increase in the liquid level is not strictly linear or even monotonic. This is because the attenuation of the signal carried in the wall over long zigzag paths will decrease not only due to interaction at the solid-liquid interface, but also due to attenuation within the solid. However, the amplitude increase due to the supplemental in-liquid paths will overshadow the attenuation of the wall-borne signal for preferred probe configurations appropriate to many common combinations of metal containers and liquids and for up to approximately a dozen bounces at a wetted interface. As a result, despite the fact that the measured response is not exactly linear, it can establish the liquid level independently of the attenuated (wall borne) signal measurement. As such, it can resolve ambiguities associated with possible residue formations.

FIGS. 15a-15d illustrate two other embodiments of this invention that distinguish among the variables effecting the transmission of the zigzag interrogating wave and minimize the undesirable influence of the non-measured variables. These embodiments are particularly useful in measuring liquid level and impedance profiles along the axis of the interrogation path. For purposes of illustration, these embodiments will be discussed with reference to the problem addressed with respect to FIG. 11, that is, determining the liquid level and interface level where there are two different liquids held in a container. As shown, FIGS. 15a and 15b each represent a segment of a probe or a wall section of a container 150a and 150b, respectively. For the purposes of relating the interaction of the ultrasonic measuring system to timing diagrams shown in FIGS. 15c and 15d, the wall sections 150a and 150b are oriented horizontally with the liquid level increasing from right to left, as indicated by an arrow labeled H. A liquid P rests on top of a liquid Q which have dissimilar densities and impedances $Z_p$ and $Z_q$, respectively. Typically $Z_q$ may be two or three times the value of $Z_p$. The dashed vertical line represented by $H_q$ represents the level of the interface between the liquids P and Q. The dashed vertical line $H_p$ represents the surface of the upper liquid P.

Figure 15A:
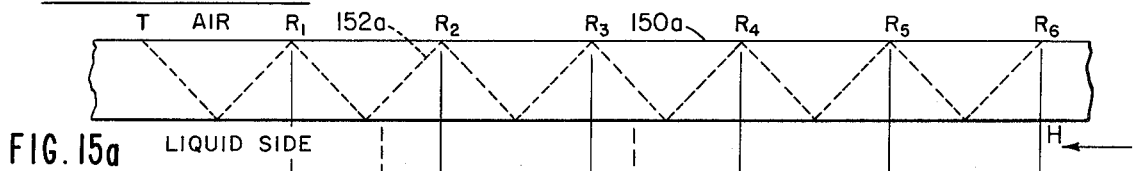
FIG. 15a is a sectional view of a transmission mode of utilizing the present invention to measure liquid level.

FIG. 15a shows a transmission mode of practicing the present invention to determine liquid level which resembles the FIG. 11 embodiment. A transmitter T located at the external or air side of the wall segment 150a launches a beam that traverses a zigzag path 152a within the wall. The beam is internally reflected at the interior or liquid side of the wall and, where the reflection point is wetted by a liquid P or Q, acoustically couples to that liquid in the manner described above with respect to FIGS. 1 and 2. A multiplicity of ultrasonic receivers, $R_1$, $R_2$,-$R_6$, are positioned at the exterior side of the wall 150a at the bounce points of the path 152a. This system is adjusted, either ultrasonically or electronically, so that the received signal amplitudes at each of the receivers $R_1$ through $R_6$ are substantially identical when the solid member 150a has air adjacent both of its sides. This situation is represented by FIG. 15c which plots the natural logarithm of the amplitude of the received signal at each of the receivers, $A_o$, $B_o$-$F_o$, as a function of time. This adjustment can be made ultrasonically by a proper selection of the transducer types or sizes or their coupling. The adjustment can also be made electronically through a proper selection of the receiver gain (in particular, using time variable gain) or through appropriate selection of shunting resistors.

When the "liquid" side of the wall segment 150a is wetted by liquids P and Q to the depths $H_p$ and $H_q$ the zig-zag interrogating wave traversing the path 152a will be attenuated. The attenuation, or the amount of energy extracted from the wave, will depend on the values of the liquid impedances $Z_p$ and $Z_q$ as well as the depths of these liquids (since the invention measures the impedances of the adjacent liquids integrated over a distributed region). The sensed pulse signals at the receivers $R_1$ through $R_6$ under this wetted condition are shown in FIG. 15d.

Figure 15B:
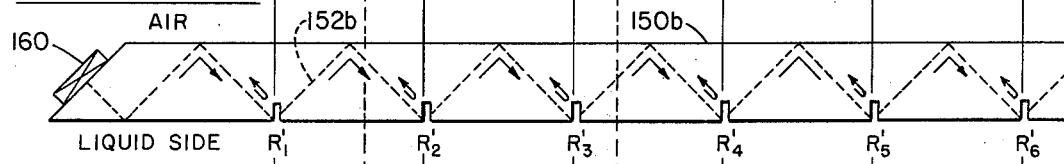
FIG. 15b is a sectional view corresponding to FIG. 15a of a reflection mode of utilizing the present invention to measure liquid level.
Figure 15C:
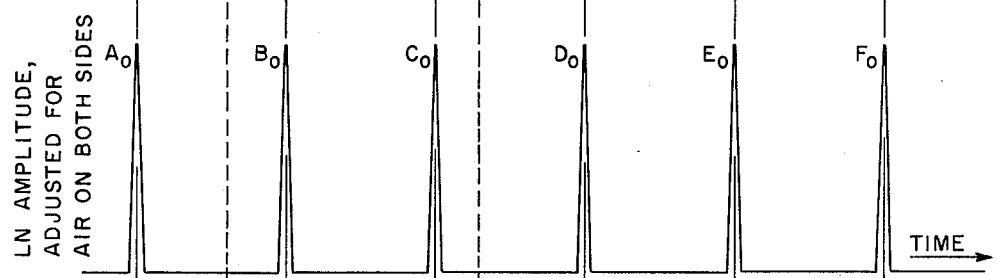
FIG. 15c is a graph corresponding to FIG. 15b plotting the natural logarithm of the amplitude of the reflected echoes as a function of time.
Figure 15D:
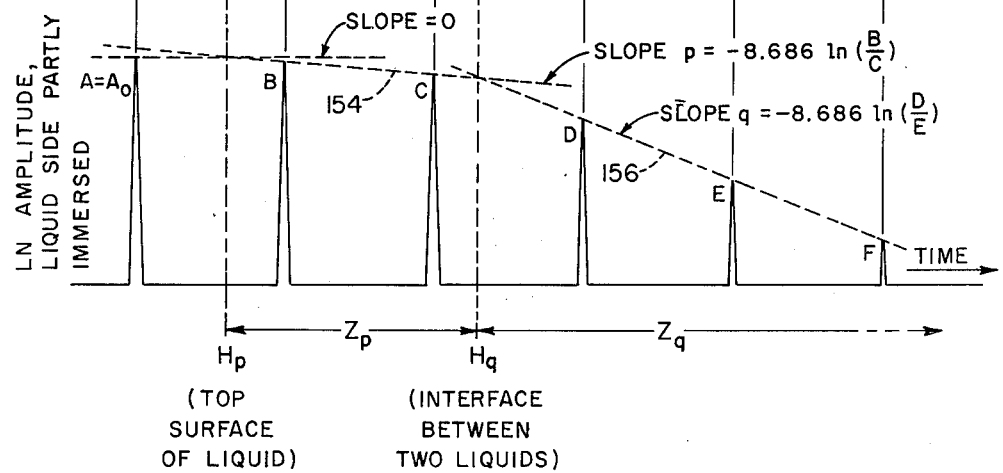
FIG. 15d is a graph corresponding to FIG. 15c showing the attenuation of the echoes when the container holds two liquids of different impedances.

FIG. 15d corresponds precisely to FIG. 15c in that it measures the same quantities on the same scale, except that the received signals, A, B,-F, in FIG. 15d are attenuated by the presence of the liquids P and Q. Because the ordinate of FIG. 15d is the natural logarithm of the amplitude of the received signal, two straight lines 154 and 156 can be drawn through the points of peak amplitude of the received signals. The line 154 is associated with the liquid P and the line 156 is associated with the liquid Q. In particular, the point of intersection between the line 154 and a horizontal line through an "unimmersed" received signal A yields an approximate indication of the top surface of the liquid P. The intersection of the lines 154 and 156 yields an approximate value for $H_q$, the interface between the liquids P and Q. Further, the slope of these tangent lines gives an approximate value for the impedances $Z_p$ and $Z_q$ of the liquids P and Q since the magnitude of the slope of these lines is approximately proportional to the acoustic impedance of the adjacent liquid. More specifically, the slope of line 154 (expressed in dB per reflector distance) is equal to $-8.686 \ln (B/C)$ and the slope of line 156 is equal to $-8.686 \ln (D/E)$, where B, C, D and E are the peak values in FIG. 15d for these signals. The slopes of these lines may be thought of as liquid induced attenuation coefficients $\alpha_p$ and $\alpha_q$ and may be expressed in units of dB per bounce, or dB per microsecond, or dB per unit distance, for example, dB per centimeter (elapsed transit time, given a constant speed of sound, being proportional to distance).

In FIG. 15d, if the distance between notches is denoted L, and if the distance that $H_q$ lies above notch D (the notch that generated echo D) is denoted h, it may be shown that $h=L[\ln (B/C)]/[\ln (D/E)]$. This algebraic expression is equivalent to the graphical method of interpolation shown in FIG. 15d. Accordingly, the location of an interface, including the top surface of a liquid, may be determined from the reflector echo amplitudes without the ambiguity or uncertainty associated with prior art approaches. Although the prior art contains examples of multi-reflector liquid level probes (see, for example, Van Valkenburg's use of surface waves along a rod with drilled holes described in U.S. Pat. No. 2,787,160 or the Krautkramer book, cited above, at page 572), it does not provide a way of interpolating between reflectors based on the amplitude of the echoes.

FIG. 15b shows another embodiment for practicing the same type of analysis described above with reference to FIG. 15a. The characterizing feature of the FIG. 15b embodiment is that it operates in a reflection mode rather than a transmission mode. More specifically, a transducer 160, coupled to an angled portion of the wall segment or probe 150b, launches an interrogating shear mode wave along a zigzag path 152b in a manner corresponding to the beam traversing the path 152a in FIG. 15a. However, the reflection or bounce points of the path 152b at the solid-liquid interface have a small notch that each generates an echo. The notches have a low reflectivity, a typical sound pressure reflection coefficient being less than 0.1. The notches are equidistantly spaced and for purposes of comparison aligned with the receivers $R_1$ through $R_6$. The notches are correspondingly denoted as $R_1'$ through $R_6'$. As in the FIG. 15a embodiment, the notch sizes or the electronics produce such echoes at each of the notches R'. At the transducer 160, received amplitudes are substantially equal when the solid wall member 150b is in air or vacuum (unwetted). When the liquids P and Q are added to the container, the interrogating beam is attenuated resulting in a received echo pattern or timing diagram as shown in FIG. 15d. It will be understood that while the embodiments have been described with reference to the measurement of the level of two liquids held in the same container using equidistant receivers or notches, the system can measure the impedance profile of a single liquid, the levels of three or more liquids, and use receivers or notches that are not equally spaced.

Each of the various embodiments described above have employed an ultrasonic system that measures either the impedance of a fluid or a liquid level using a moderately directional, bulk SV mode sound waves that are propagated along a zigzag path in a homogeneous, flaw-free solid member. Common to all of these embodiments is the concept that if the zigzag SV wave reflects from a wetted interface, and if the angle of incidence of the wave exceeds the first critical angle by at least five degrees and is less than the second critical angle by at least 10 degrees, then the attenuation of the zigzag wave provides the desired measurement. As described above, the solid member can either be an elongated probe which is separate from the container that holds the fluid or liquid under investigation (as described with reference to FIGS. 3a–3g, 11 and 14) or it can be a portion of the wall of the container with the path in the wall portion being vertical, circumferential, or oblique (as described with reference to FIGS. 4–9, 11–13, and 15a–15d). It should also be noted that the embodiments of FIGS. 3a–9 can be used to measure either the impedance of a given fluid or liquid level. In contrast, the embodiments described with reference to FIGS. 11–15d are principally directed to the measurement of liquid level.

It will also be apparent from the foregoing description that a significant aspect of the present invention includes features for separating the many variables effecting the measurement. The invention measures a selected variable (e.g. liquid level) while rendering the measurement relatively insensitive to other variables such as the non-measured parameter (impedance), residues, changes of temperature of the solid or the liquid, changes in the impedance of the liquid, the presence of multiple liquids, and the viscosity of the measured liquid. The principal form for this variable separation is the provision of the supplemental reference path in the ultrasonic system. This supplemental path, as noted above, can take a wide variety of forms. For example, in FIG. 3f the notch 26 provided a reference echo to allow compensation for changes in the temperature of the probe itself. In FIG. 5, auxiliary paths 54 and 54a which are always immersed or not immersed, respectively, provide the desired reference information to separate variables. FIG. 5 also discloses the use of interrogating paths that are parallel or oblique to the surface of the level to make the liquid level determination relatively insensitive to changes in the impedance of the liquid. FIGS. 8 and 12–14 disclose the use of in-liquid paths. FIGS. 11 and 15a–15d disclose embodiments utilizing multiple receivers or reflective notches to measure liquid level. The FIG. 11 system uses a zigzag interrogation at a remote tip of a probe to provide a measurement of the impedance of the liquid at that point. In contrast, in the FIG. 15a–15d embodiments the interrogating wave pursues a zigzag path throughout its length with the notches being positioned at the points of reflection from the solid-liquid interface. Further arrangements for providing an isolation of variables include a system of spectral analysis described with reference to FIG. 10, separate interrogating frequencies over separate paths as described with reference to FIGS. 12 and 13, and the use of scattering or absorptive regions intermediate the anticipated bounce points of the zigzag interrogating wave to avoid ambiguity in the received signal.

As is evident, the invention has a wide range of applications and methods of implementation many of which have been described in detail. It will be recognized however, that these and various other modifications and alterations of the invention will become apparent to those skilled in the art from the foregoing detailed description and the accompanying drawings. Such modifications are intended to fall within the scope of the appended claims.

What is claimed and desired to be secured by Letters Patent is:

1. An ultrasonic system for measuring at least one selected impedance related parameter of a fluid comprising
   a solid member capable of supporting the propagation of moderately directional, bulk SV shear waves without mode conversion,
   transducer means acoustically coupled to said member for generating and detecting said SV waves propagated along a multiply-reflected path that includes at least two reflections in a region of said member remote from said transducer means and is at least partially immersed in said fluid to form a solid-fluid interface, said reflections having an angle of incidence that exceeds the first critical angle by at least five degrees and is at least ten degrees less than the second critical angle, said path lying in a portion of said member that is substantially homogeneous and flaw free and said SV waves having a frequency that lies in the range of 0.5 to 5 MHz to minimize energy loss by absorption and maximize energy loss by coupling to said fluid at said reflections in said remote region, and means for sensing the attenuation of said waves along said path at said interface to measure said selected impedance related parameter.

2. An ultrasonic measuring system according to claim 1 wherein the number N of said reflections in said remote region is in the range of 2 to 100.

3. An ultrasonic measuring system according to claim 2 wherein N is sufficiently large that the product of N and the reflection loss coefficient $R_L$ at said reflections in said remote region is at least 20 dB.

4. An ultrasonic measuring system according to claim 2 wherein said angle of incidence is about 45° and where N is substantially equal to the acoustic impedance ratio.

5. An ultrasonic measuring system according to claim 2 wherein said solid member is an elongated rod having said transducer means coupled to one end of said rod and having said remote region disposed at the opposite end of said rod separated from said one end by a buffer portion of said solid member.

6. An ultrasonic measuring system according to claim 5 wherein said remote region is separated from said transducer means by distance at least equal to 30 $\lambda$ where $\lambda$ is the wavelength of said SV waves.

7. An ultrasonic measuring system according to claim 5 wherein said remote region is localized.

8. An ultrasonic measuring system according to claim 7 wherein said localized remote region comprises at least two surfaces beveled with respect to the longitudinal axis of said rod.

9. An ultrasonic measuring system according to claim 7 wherein said rod has at least two localized remote regions axially spaced from one another.

10. An ultrasonic measuring system according to claim 6 wherein said remote region is distributed.

11. An ultrasonic measuring system according to claim 10 wherein said distributed remote region supports at least ten of said reflections.

12. An ultrasonic measuring system according to claim 10 wherein said transducer means and said buffer portion are shielded from said fluid.

13. An ultrasonic measuring system according to claim 12 wherein said remote region is protectively coated at least in part with an elastically dissimilar material whose thickness is less than one-tenth of a wavelength.

14. An ultrasonic measuring system according to claim 2 wherein said solid member is a wall segment of a container for said fluid and said remote region is one surface of said wall segment.

15. An ultrasonic measuring system according to claim 2 wherein said angle of incidence is in the range of 45° to 60°.

16. An ultrasonic measuring system according to claim 2 wherein said fluid is a liquid that has a kinematic viscosity of less than 10 stokes.

17. An ultrasonic measuring system according to claim 1 wherein said transducer means is permanently bonded to said member.

18. An ultrasonic system for measuring at least one selected impedance related parameter of a fluid comprising a solid member capable of supporting the propagation of moderately directional, bulk SV shear waves without mode conversion, first transducer means acoustically coupled to said member for generating and detecting at least said SV waves propagated along a multiply-reflected first path that includes at least two reflections in a region of said member remote from said transducer means and is at least partially immersed in said fluid to form a solid-fluid interface, said reflection having an angle of incidence that exceeds the first critical angle by at least five degrees and is at least ten degrees less than the second critical angle, said first path lying in a portion of said member that is substantially homogeneous and flaw free and said SV waves having a frequency that lies in the range of 0.5 to 5 MHz to minimize energy loss by absorption and maximize energy loss by coupling to said fluid at said reflections in said remote region, means for sensing the attenuation of said waves along said first path at said interface to measure said selected impedance related parameter, and desensitizing means for rendering said measurement substantially insensitive to variations in other parameters which could influence said measurement.

19. An ultrasonic measuring system according to claim 18 wherein said desensitizing means comprises a supplemental ultrasonic reference path.

20. An ultrasonic measuring system according to claim 19 whrein said first and reference paths enter and exit said solid member at the same interfaces and wherein said first path traverses said interface at an oblique angle of incidence and said reference path traverses said interface at a substantially normal angle of incidence.

21. An ultrasonic measuring system as in claim 19 wherein said first path is interrogated in a through-transmission mode and said reference path is interrogated in a pulse-echo mode.

22. An ultrasonic measuring system according to claim 19 wherein said sensing means responds to differences in the transmission times over said first path and said reference path.

23. An ultrasonic measuring system according to claim 19 wherein a portion of said reference path is propagated in the fluid being measured.

24. An ultrasonic measuring system according to claim 23 wherein said first path and said reference path are interrogated at at least two different frequencies to distinguish between the waves received along said paths by said sensing means.

25. An ultrasonic measuring system according to claim 23 wherein said solid member comprises a pair of elongated probes in parallel spaced relationship that measure the level of said liquid between said probes.

26. An ultrasonic measuring system according to claim 18 wherein said reference path lies at least partially in a solid material which is substantially the same as that of said solid member.

27. An ultrasonic measuring system according to claim 26 wherein said reference path lies within said solid member and is not reflected at an oblique angle of incidence.

28. An ultrasonic measuring system according to claim 27 where said solid member includes a reflective notch which generates as said reference path an echo transmitted generally along the axis of said first path.

29. An ultrasonic measuring system according to claim 18 further comprising
second transducer means acoustically coupled to said solid material for generating and detecting said supplemental reference path and wherein the coupling of said first and second transducer means to said solid member and said solid material, respectively, have a known transmission efficiency.

30. An ultrasonic measuring system according to claim 29 wherein said first and second transducer means each include at least one transducer common to both said multiply-reflected first path and said reference path.

31. An ultrasonic measuring system according to claim 30 wherein said first and second transducer means use the same transducers.

32. An ultrasonic measuring system according to claim 30 wherein said at least one transducer common to said first and reference paths is coupled to said solid member through a wedge that propagates said SV waves.

33. An ultrasonic measuring system according to claim 18 wherein said fluid is a liquid held in a container, said solid member is a wall segment of said container, said measured impedance related parameter is its liquid level, and said desensitizing means comprises a plurality of second transducer assemblies located at an unwetted side of said solid member and at reflection points of said multiply-reflected first path.

34. An ultrasonic measuring system according to claim 33 wherein said second transducer assemblies are adjusted so that the detected wave at each of said assemblies has substantially an equal amplitude when said solid member is unwetted.

35. An ultrasonic measuring system according to claim 18 wherein said fluid is a liquid held in a container, said solid member is a wall segment of said container, said measured impedance related parameter is its liquid level, and said desensitization means comprises a plurality of reflective means located at an unwetted side of said solid member and at reflection points of said multiply-reflected first path.

36. An ultrasonic measuring system according to claim 35 wherein said reflective means comprises a dummy reflector wedge.

37. An ultrasonic measuring system according to claim 35 wherein said reflective means comprises a notch formed in said solid member.

38. An ultrasonic measuring system according to claim 37 wherein said solid member comprises at least one elongated probe.

39. An ultrasonic measuring system according to claim 18 wherein said fluid is a liquid and said desensitizing means comprises means for generating reflective echoes that propagate along the axis of said first path.

40. The ultrasonic measuring system according to claim 39 wherein said echo generating means comprises a series of notches formed on the side of said solid member adjacent said liquid.

41. The ultrasonic measuring system according to claim 40 wherein said notches are structured to generate echoes of equal amplitude when said solid member is unwetted.

42. An ultrasonic measuring system according to claim 41 wherein the fluid is comprised of two fluids P and Q of dissimilar impedances $Z_p$ and $Z_q$, wherein said selected impedance related parameter is the location of an interface between the fluids P and Q, and wherein said sensing means responds to the relative amplitudes of successive echoes generated at said notches which in turn yields said interface location.

43. An ultrasonic measuring system according to claim 40 wherein said solid member is an elongated rod having said transducer means coupled to said one end of said rod and having said remote region disposed at the opposite end of said rod separated from said one end by a buffer portion of said rod.

44. An ultrasonic measuring system according to claim 43 wherein said remote region has two mutually inclined double surfaces adjacent said liquid to generate two of said reflections.

45. An ultrasonic measuring system according to claim 18 wherein said fluid is a liquid and said densensitizing means comprises orienting the axis of said multiply-reflected first path obliquely with respect to the surface of said liquid.

46. An ultrasonic measuring system according to claim 45 wherein said desensitizing means comprises at least one additional compensation path that is fully immersed in said liquid.

47. An ultrasonic measuring system according to claim 45 wherein said desensitizing means comprises at least one additional compensation path that is not immersed in said liquid.

48. An ultrasonic measuring system according to claim 38 or 45 wherein said compensation path is generally the same as said first path and includes the same number of reflections at the solid-fluid interface.

49. An ultrasonic measuring system according to claim 18 wherein said fluid is a liquid and said desensitizing means comprises orienting the axis of said first path parallel to the surface of said liquid.

50. An ultrasonic measuring system according to claim 18 wherein said desensitizing means comprises means for dissipating incident acoustic energy intermediate adjacent reflection points of said first path.

51. An ultrasonic measuring system according to claim 50 wherein said dissipating means comprises acoustic energy scattering means.

52. An ultrasonic measuring system according to claim 50 wherein said dissipating means comprises an absorptive material secured to the surface of said solid member.

53. An ultrasonic measuring system according to claim 18 wherein said desensitizing means comprises means for operating said first transducer means at different frequencies to compare the frequency response of said system.

54. An ultrasonic measuring system according to claims 5, 6, 7 or 8 wherein said elongated rod is truncated along a plane that is substantially perpendicular to shear waves generated by said transducer means to produce a shear wave echo that is received at said sensing means prior to said SV waves propagated along said multiply-reflected path.

* * * * *

UNITED STATES PATENT AND TRADEMARK OFFICE
CERTIFICATE OF CORRECTION

PATENT NO. : 4,320,659
DATED : March 23, 1982
INVENTOR(S) : Lawrence C. Lynnworth, John L. Seger, James E. Bradshaw It is certified that error appears in the above-identified patent and that said Letters Patent are hereby corrected as shown below:

Column 9, line 9, "$\div_s = 45°$" should be --$\theta_s = 45°$--;

Column 9, line 34, "arrangement" should be --arrangements--;

Column 12, line 39, "within" should be --_within_--;

*Column 17, line 19, "Fig." should read --Figs.--;

Column 20, line 35, "15a-15b" should read --15a-15d--;

Column 22, lines 26-31, "These...130" should not be italicized;

Column 23, line 44, "15a-15d" should read --15a-15b--.

Signed and Sealed this

Third Day of August 1982

[SEAL]

Attest:

Attesting Officer

GERALD J. MOSSINGHOFF
*Commissioner of Patents and Trademarks*